US009696131B2

(12) United States Patent
Montag et al.

(10) Patent No.: US 9,696,131 B2
(45) Date of Patent: Jul. 4, 2017

(54) ADAPTIVE FLUOROSCOPE LOCATION FOR THE APPLICATION OF FIELD COMPENSATION

(71) Applicant: BIOSENSE WEBSTER (ISRAEL) LTD., Yokneam (IL)

(72) Inventors: Avram Dan Montag, Haifa (IL); Meir Bar-Tal, Haifa (IL)

(73) Assignee: Biosense Webster (ISRAEL) Ltd., Yokneam (IL)

( * ) Notice: Subject to any disclaimer, the term of this patent is extended or adjusted under 35 U.S.C. 154(b) by 721 days.

(21) Appl. No.: 14/140,112

(22) Filed: Dec. 24, 2013

(65) Prior Publication Data

US 2015/0176961 A1    Jun. 25, 2015

(51) Int. Cl.
*G01C 17/38* (2006.01)
*G01B 7/14* (2006.01)
(Continued)

(52) U.S. Cl.
CPC .............. *G01B 7/14* (2013.01); *A61B 5/062* (2013.01); *A61B 5/065* (2013.01); *A61B 90/36* (2016.02);
(Continued)

(58) Field of Classification Search
CPC .......... G01B 7/14; G01B 7/004; A61B 90/36; A61B 5/062; A61B 5/065; A61B 5/6852;
(Continued)

(56) References Cited

U.S. PATENT DOCUMENTS 5,274,551 A    12/1993  Corby, Jr.
5,546,951 A    8/1996   Ben Haim
(Continued)

FOREIGN PATENT DOCUMENTS

EP    1658818 A1    5/2006
EP    2168478       3/2010
(Continued)

OTHER PUBLICATIONS

EP Search Report EP14200175.9 dated Apr. 16, 2015.
(Continued)

*Primary Examiner* — Roy Y Yi
(74) *Attorney, Agent, or Firm* — Louis J. Capezzuto

(57) ABSTRACT

Compensation for a field-perturbing element in a magnetic tracking system for locating a probe is achieved by creating a reaction field model while the field-perturbing element is in known positions. A magnetic field location sensor is disposed between the field-perturbing element and magnetic field generators of the tracking system. Magnetic field readings from the location sensor and from a magnetic field sensor on the probe are taken while the field-perturbing element is present. The position of the field-perturbing element is estimated from the location sensor readings, and a predicted reaction field calculated from the reaction field model. A compensated measurement is obtained by subtracting the predicted reaction field from the field detected by the location sensor. The readings from the probe sensor are adjusted using the compensated measurement in order to calculate the true position of the probe.

23 Claims, 14 Drawing Sheets

(51) Int. Cl.
*G01B 7/004* (2006.01)
*G01D 18/00* (2006.01)
*A61B 5/06* (2006.01)
*A61B 90/00* (2016.01)
*A61B 5/00* (2006.01)
*A61B 34/20* (2016.01)

(52) U.S. Cl.
CPC .............. *G01B 7/004* (2013.01); *G01D 18/00* (2013.01); *A61B 5/6852* (2013.01); *A61B 2034/2051* (2016.02)

(58) Field of Classification Search
CPC ...... A61B 2034/2051; A61B 2090/374; A61B 2090/3782; A61B 2090/3904; A61B 2090/3925; A61B 2090/3933; A61B 2090/3941; A61B 2090/395; A61B 2090/3954; A61B 2090/3958; A61B 2090/3987; A61B 2090/3995; A61B 2218/008; G01D 18/00
USPC .......................................................... 702/94
See application file for complete search history.

(56) References Cited

U.S. PATENT DOCUMENTS

| | | | |
|---|---|---|---|
| 5,738,096 | A | 4/1998 | Ben Haim |
| 6,226,542 | B1 | 5/2001 | Reisfeld |
| 6,301,496 | B1 | 10/2001 | Reisfeld |
| 6,690,963 | B2 | 2/2004 | Ben Haim |
| 6,814,733 | B2 | 11/2004 | Schwartz |
| 6,892,091 | B1 | 5/2005 | Ben Haim |
| 6,997,924 | B2 | 2/2006 | Schwartz |
| 7,156,816 | B2 | 1/2007 | Schwartz |
| 7,536,218 | B2 | 5/2009 | Govari et al. |
| 7,756,576 | B2 | 7/2010 | Levin |
| 8,303,505 | B2 | 11/2012 | Webler et al. |
| 8,456,182 | B2 | 6/2013 | Bar-Tal et al. |
| 8,478,383 | B2 | 7/2013 | Bar-Tal et al. |
| 2005/0024043 | A1 | 2/2005 | Govari |
| 2007/0270692 | A1 | 11/2007 | Barbu et al. |
| 2007/0276227 | A1 | 11/2007 | Boese |
| 2009/0076483 | A1 | 3/2009 | Danehorn |
| 2009/0135992 | A1 | 5/2009 | Vaillant et al. |
| 2010/0082280 | A1 | 4/2010 | Schneider |
| 2011/0088890 | A1* | 4/2011 | Clark ................ E21B 47/02216 166/66.5 |
| 2012/0165656 | A1 | 6/2012 | Montag et al. |
| 2012/0172712 | A1 | 7/2012 | Bar-Tal |
| 2012/0232384 | A1 | 9/2012 | Wu et al. |
| 2013/0072788 | A1 | 3/2013 | Wu et al. |
| 2013/0231556 | A1 | 9/2013 | Holsing et al. |
| 2013/0331687 | A1 | 12/2013 | Liao et al. |
| 2014/0221803 | A1 | 8/2014 | Bar-Tal et al. |

FOREIGN PATENT DOCUMENTS

| | | |
|---|---|---|
| EP | 2732765 | 8/2014 |
| WO | WO 96/05768 A1 | 2/1996 |
| WO | WO 2007/138492 | 12/2007 |
| WO | WO 2013/036831 | 3/2013 |
| WO | WO 2013/057641 | 4/2013 |
| WO | WO 2014/124447 | 8/2014 |

OTHER PUBLICATIONS

Felsberg, M. et al. The Monogenic Signal, IEEE Transactions on Signal Processing. vol. 49, No. 12, Dec. 2011, pp. 3136-3144.

Loy, G. et al. A Fast Radial Symmetry Transform for Detecting Points of Interest. IEEE Transactions on Pattern Analysis and Machine Intelligence, Australian National University, Aug. 2003.

Landau, L.D. et al., Electrodynamics of Continuous Media. Pergamon Press (1960) vol. 8, Sec. 45., pp. 189-190. Course of Theoretical Physics, Textbook: ISBN No. 0-08-09105-9.

Lindell, I.V. et al., Magnetostratic Image Theory for the Premeable Sphere, IEEE Transactions on Magnetics, (Jul. 1992) vol. 28, No. 4, pp. 1930-1934.

Extended European Search Report for EP16155496.9 Application, Dated Jul. 6, 2016.

Extended European Search Report for EP16155431.6 Application, Dated Jun. 29, 2016.

* cited by examiner $$\text{vec}(B_{reaction}(\text{red})) = (B_{Transmitted}(\text{blue}))^T \otimes T_{sph}(\text{red}_{green\ centered}) \cdot \text{vec}(T_{reac})$$

FIG. 7

$$\begin{bmatrix} \text{vec}(B_{reaction}(\text{red}))^{Loc1} \\ \vdots \\ \text{vec}(B_{reaction}(\text{red}))^{LocN} \end{bmatrix} = \begin{bmatrix} (B_{Transmitted}(\text{blue}))^T \otimes T_{sph}(\text{red}_{green\ centered})^{Loc1} \\ \vdots \\ (B_{Transmitted}(\text{blue}))^T \otimes T_{sph}(\text{red}_{green\ centered})^{LocN} \end{bmatrix} \cdot \text{vec}(T_{reac})$$

FIG. 8

$$[B_{reac}(x_{CARTO}, y_{CARTO}, z_{CARTO})] = Rot_{det}^{CARTO} \cdot ([T_{spatial}^{det}(x_{det}, y_{det}, z_{det})] \cdot [T_{reaction}^{det}] \cdot [B_{satellite}^{det}]$$
$$+ Rot_{col}^{CARTO} \cdot ([T_{spatial}^{col}(x_{col}, y_{col}, z_{col})] \cdot [T_{reaction}^{col}] \cdot [B_{satellite}^{col}] \quad (5)$$

$$\begin{bmatrix} \text{vec}[B_{reaction}^{j=1}] \\ \vdots \\ \text{vec}[B_{reaction}^{j=M}] \end{bmatrix} = \begin{bmatrix} \left(\left(B_{satellite}^{det}\right)^T \otimes T_{spatial}^{det}\right)^{j=1} \\ \vdots \\ \left(\left(B_{satellite}^{det}\right)^T \otimes T_{spatial}^{det}\right)^{j=M} \end{bmatrix} \cdot \text{vec}[T_{reaction}^{det}]$$

$$+ \begin{bmatrix} \left(\left(B_{satellite}^{col}\right)^T \otimes T_{spatial}^{col}\right)^{j=1} \\ \vdots \\ \left(\left(B_{satellite}^{col}\right)^T \otimes T_{spatial}^{col}\right)^{j=M} \end{bmatrix} \cdot \text{vec}[T_{reaction}^{col}] \quad (10)$$

$$\begin{bmatrix} \text{vec}[B_{reaction}^{j=1}] \\ \vdots \\ \text{vec}[B_{reaction}^{j=M}] \end{bmatrix} = \begin{bmatrix} \left( \left( B_{satellite}^{det} \right)^T \otimes T_{spatial}^{det} \right)^{j=1} & \left( \left( B_{satellite}^{col} \right)^T \otimes T_{spatial}^{col} \right)^{j=1} \\ \vdots & \vdots \\ \left( \left( B_{satellite}^{det} \right)^T \otimes T_{spatial}^{det} \right)^{j=M} & \left( \left( B_{satellite}^{col} \right)^T \otimes T_{spatial}^{col} \right)^{j=M} \end{bmatrix} \begin{bmatrix} \text{vec}[T_{reaction}^{det}] \\ \text{vec}[T_{reaction}^{col}] \end{bmatrix} \quad (11)$$

FIG. 14

ADAPTIVE FLUOROSCOPE LOCATION FOR THE APPLICATION OF FIELD COMPENSATION

BACKGROUND OF THE INVENTION

1. Field of the Invention

This invention relates to sensing the position of an object placed within a living body. More particularly, this invention relates to improvements in a catheter tracking system.

2. Description of the Related Art

The meanings of certain acronyms and abbreviations used herein are given in Table 1.

TABLE 1

| Acronyms and Abbreviations | |
|---|---|
| FER | Fluoroscopic Effect. Reduction |
| LAO | Left. Anterior-Oblique |
| LP | Location Pad |
| RAO | Right Anterior-Oblique |
| SID | Source-to-Image Distance |

A wide range of medical procedures involve placing objects, such as sensors, tubes, catheters, dispensing devices, and implants, within the body. Real-time imaging methods are often used to assist doctors in visualizing the object and its surroundings during these procedures. Some methods track the objects using the object using magnetic fields. However, disturbances in the magnetic field may create tracking errors.

Catheters are frequently inserted into patients while using an x-ray fluoroscope to monitor the process in conjunction with a magnetic tracking system. During the procedure, the fluoroscope may be activated as an extra visual check on anatomic maps that may be available or concurrently produced, and in order to view other instruments that may be internally situated within a patient. To that end operators prefer to place the detector as close to the patient as possible. This minimizes the radiation dose to the staff and maximizes the size of the projected images. However, when the fluoroscope detector is placed too near to the patient, its metallic components distort the magnetic field measurements, which are essential to the magnetic tracking system. The distortion causes the magnetic tracking system to report apparent location and orientation shifts from their true values. Translational shifts can reach several centimeters, and rotational shifts can be as large as several degrees. Such shifts could or cause the operator to lose confidence in the magnetic tracking system or even mislead an operator who was unaware of the distortion.

U.S. Pat. No. 6,147,480, to Osadchy et al., whose disclosure is incorporated herein by reference, describes a method for tracking an object using energy fields in the presence of interference due to introduction of an article responsive to the fields, and in the vicinity of the object.

U.S. Patent Application Publication No. 2012/0165656 to Montag et al., which is commonly assigned and herein incorporated by reference, describes generating, using a plurality of magnetic transmitters, a magnetic field in a region and introducing a field-perturbing element into the region. The method includes characterizing multiple images of each magnetic transmitter in the field-perturbing element, and calculating a reaction magnetic field in the region based on the characterized images. The method further includes positioning a probe in the region and measuring a perturbed magnetic field at the probe, and determining a location of the probe in response to the measured perturbed magnetic field and the calculated reaction magnetic field. The method described in U.S. Patent Application Publication No. 2012/0165656 is based on a spatial transfer matrix as set forth in paragraphs and FIGS. 8A to 8G of this reference.

An example of the spatial transfer matrix in U.S. Patent Application Publication No. 2012/0165656 is $T_{spatial}(x,y,z)$. As described in U.S. Patent Application Publication No. 2012/0165656, $T_{spatial}(x,y,z)$ is a 3×15 spatial transfer matrix that is derived from spherical harmonic terms, and is calculated from the following exemplary equations A-O as set forth in FIGS. 8A to 8G of this reference and outlined below:

$$\frac{\sqrt{\frac{3}{\pi}}\,xz}{2(x^2+y^2+z^2)^{5/2}} \qquad \text{Equation A - Column 1}$$

$$\frac{\sqrt{\frac{3}{\pi}}\,yz}{2(x^2+y^2+z^2)^{5/2}}$$

$$-\frac{x^2+y^2-2z^2}{2\sqrt{3\pi}\,(x^2+y^2+z^2)^{5/2}}$$

$$\frac{-2x^2+y^2+z^2}{2\sqrt{6\pi}\,(x^2+y^2+z^2)^{5/2}} \qquad \text{Equation B - Column 2}$$

$$-\frac{\sqrt{\frac{3}{2\pi}}\,xy}{2(x^2+y^2+z^2)^{5/2}}$$

$$-\frac{\sqrt{\frac{3}{2\pi}}\,xz}{2(x^2+y^2+z^2)^{5/2}}$$

$$-\frac{\sqrt{\frac{3}{2\pi}}\,xy}{2(x^2+y^2+z^2)^{5/2}} \qquad \text{Equation C - Column 3}$$

$$\frac{x^2-2y^2+z^2}{2\sqrt{6\pi}\,(x^2+y^2+z^2)^{5/2}}$$

$$-\frac{\sqrt{\frac{3}{2\pi}}\,yz}{2(x^2+y^2+z^2)^{5/2}}$$

$$-\frac{3x(x^2+y^2-4z^2)}{4\sqrt{5\pi}\,(x^2+y^2+z^2)^{7/2}} \qquad \text{Equation D - Column 4}$$

$$-\frac{3y(x^2+y^2-4z^2)}{4\sqrt{5\pi}\,(x^2+y^2+z^2)^{7/2}}$$

$$\frac{6z^3-9(x^2+y^2)z}{4\sqrt{5\pi}\,(x^2+y^2+z^2)^{7/2}}$$

$$\frac{\sqrt{\frac{3}{10\pi}}\,z(-4x^2+y^2+z^2)}{2(x^2+y^2+z^2)^{7/2}} \qquad \text{Equation E - Column 5}$$

$$-\frac{\sqrt{\frac{15}{2\pi}}\,xyz}{2(x^2+y^2+z^2)^{7/2}}$$

$$\frac{\sqrt{\frac{3}{10\pi}}\,x(x^2+y^2-4z^2)}{2(x^2+y^2+z^2)^{7/2}}$$

-continued

Equation F - Column 6

$$-\frac{\sqrt{\frac{3}{10\pi}}\, y(-4x^2 + y^2 + z^2)}{2(x^2 + y^2 + z^2)^{7/2}}$$

$$-\frac{\sqrt{\frac{3}{10\pi}}\, x(x^2 - 4y^2 + z^2)}{2(x^2 + y^2 + z^2)^{7/2}}$$

$$\frac{\sqrt{\frac{15}{2\pi}}\, xyz}{2(x^2 + y^2 + z^2)^{7/2}}$$

Equation G - Column 7

$$-\frac{\sqrt{\frac{15}{2\pi}}\, xyz}{2(x^2 + y^2 + z^2)^{7/2}}$$

$$\frac{\sqrt{\frac{3}{10\pi}}\, z(x^2 - 4y^2 + z^2)}{2(x^2 + y^2 + z^2)^{7/2}}$$

$$\frac{\sqrt{\frac{3}{10\pi}}\, y(x^2 + y^2 - 4z^2)}{2(x^2 + y^2 + z^2)^{7/2}}$$

Equation H - Column 8

$$-\frac{\sqrt{\frac{3}{10\pi}}\, y(-4x^2 + y^2 + z^2)}{2(x^2 + y^2 + z^2)^{7/2}}$$

$$-\frac{\sqrt{\frac{3}{10\pi}}\, x(x^2 - 4y^2 + z^2)}{2(x^2 + y^2 + z^2)^{7/2}}$$

$$\frac{\sqrt{\frac{15}{2\pi}}\, xyz}{2(x^2 + y^2 + z^2)^{7/2}}$$

Equation I - Column 9

$$\frac{5xz(4z^2 - 3(x^2 + y^2))}{4\sqrt{7\pi}\,(x^2 + y^2 + z^2)^{9/2}}$$

$$\frac{5yz(4z^2 - 3(x^2 + y^2))}{4\sqrt{7\pi}\,(x^2 + y^2 + z^2)^{9/2}}$$

$$\frac{8z^4 - 24(x^2 + y^2)z^2 + 3(x^2 + y^2)^2}{4\sqrt{7\pi}\,(x^2 + y^2 + z^2)^{9/2}}$$

Equation J - Column 10

$$\frac{\sqrt{\frac{3}{7\pi}}\,(4x^4 + 3(y^2 - 9z^2)x^2 - y^4 + 4z^4 + 3y^2 z^2)}{8(x^2 + y^2 + z^2)^{9/2}}$$

$$\frac{5\sqrt{\frac{3}{7\pi}}\, xy(x^2 + y^2 - 6z^2)}{8(x^2 + y^2 + z^2)^{9/2}}$$

$$\frac{5\sqrt{\frac{3}{7\pi}}\, xz(3(x^2 + y^2) - 4z^2)}{8(x^2 + y^2 + z^2)^{9/2}}$$

Equation K - Column 11

$$\frac{\sqrt{\frac{15}{14\pi}}\, xz(5x^2 - 9y^2 - 2z^2)}{4(x^2 + y^2 + z^2)^{9/2}}$$

$$\frac{\sqrt{\frac{15}{14\pi}}\, yz(9x^2 - 5y^2 + 2z^2)}{4(x^2 + y^2 + z^2)^{9/2}}$$

$$-\frac{\sqrt{\frac{15}{14\pi}}\,(x - y)(x + y)(x^2 + y^2 - 6z^2)}{4(x^2 + y^2 + z^2)^{9/2}}$$

Equation L - Column 12

$$\frac{\sqrt{\frac{5}{7\pi}}\,(-4x^4 + 3(7y^2 + z^2)x^2 - 3y^2(y^2 + z^2))}{8(x^2 + y^2 + z^2)^{9/2}}$$

$$-\frac{\sqrt{\frac{5}{7\pi}}\, xy(13x^2 + 15y^2 + 6z^2)}{8(x^2 + y^2 + z^2)^{9/2}}$$

$$-\frac{\sqrt{\frac{35}{\pi}}\, x(x^2 - 3y^2)z}{8(x^2 + y^2 + z^2)^{9/2}}$$

Equation M - Column 13

$$\frac{5\sqrt{\frac{3}{7\pi}}\, xy(x^2 + y^2 - 6z^2)}{8(x^2 + y^2 + z^2)^{9/2}}$$

$$\frac{\sqrt{\frac{3}{7\pi}}\,(-x^4 + 3(y^2 + z^2)x^2 + 4y^4 + 4z^4 - 27y^2 z^2)}{8(x^2 + y^2 + z^2)^{9/2}}$$

$$\frac{5\sqrt{\frac{3}{7\pi}}\, yz(3(x^2 + y^2) - 4z^2)}{8(x^2 + y^2 + z^2)^{9/2}}$$

Equation N - Column 14

$$-\frac{\sqrt{\frac{15}{14\pi}}\, yz(-6x^2 + y^2 + z^2)}{2(x^2 + y^2 + z^2)^{9/2}}$$

$$-\frac{\sqrt{\frac{15}{14\pi}}\, xz(x^2 - 6y^2 + z^2)}{2(x^2 + y^2 + z^2)^{9/2}}$$

$$-\frac{\sqrt{\frac{15}{14\pi}}\, xy(x^2 + y^2 - 6z^2)}{2(x^2 + y^2 + z^2)^{9/2}}$$

Equation O - Column 15

$$\frac{\sqrt{\frac{5}{7\pi}}\, xy(-15x^2 + 13y^2 + 6z^2)}{8(x^2 + y^2 + z^2)^{9/2}}$$

$$\frac{\sqrt{\frac{5}{7\pi}}\,(3x^4 + 3(z^2 - 7y^2)x^2 + 4y^4 - 3y^2 z^2)}{8(x^2 + y^2 + z^2)^{9/2}}$$

$$\frac{\sqrt{\frac{35}{\pi}}\, y(y^2 - 3x^2)z}{8(x^2 + y^2 + z^2)^{9/2}}.$$

SUMMARY OF THE INVENTION

Some current magnetic tracking systems, for example the CARTO® 3 System, available from Biosense Webster, Inc., 3333 Diamond Canyon Road, Diamond Bar, Calif. 91765, currently have an internal mechanism for detecting metal interference. Typically, above a certain threshold, corresponding to estimated location errors of 5 mm for catheters inside the heart, the system warns the operator. Location errors greater than 5 mm can lead to inaccurate maps, thereby rendering the system ineffective and possibly harmful. The mitigation is to move the fluoroscope detector farther from the patient's chest. There is a second threshold corresponding to average locations errors of 20 mm, where the system will not allow the use of the acquired data in making a map of the cardiac activity. While useful, such internal warning mechanisms may have a significant margin of error, and cannot be relied upon to compensate for the above-mentioned distortional effects. Consequently, more sophisticated location error detection techniques are desirable.

Embodiments of the invention compensate for location tracking errors while eliminating the need for provisions for coordination between the magnetic tracking system and the fluoroscope. Such coordination heretofore was required to inform the magnetic tracking system of the location and orientation of the fluoroscope components in order to properly compensate for the tracking errors.

There is provided according to embodiments of the invention a method, which is carried out in a calibration phase by generating a magnetic field in a region using a plurality of magnetic field generators, placing a field-perturbing element in known positions within the region, and creating a reaction field model by calculating respective reaction magnetic fields while the field-perturbing element is in the known positions.

The method is further carried out in an operational phase by placing the field-perturbing element in a new position within the region, disposing a magnetic field location sensor between the field-perturbing element and the magnetic field generators, and introducing a distal segment of a probe into the region. A probe magnetic field sensor is disposed on the distal segment. The method is further carried out by regenerating a perturbed magnetic field with the magnetic field generators, obtaining first measurements of the perturbed magnetic field from the probe magnetic field sensor, obtaining second measurements of the perturbed magnetic field from the location sensor, reconstructing the new position of the field-perturbing element from the second measurements, obtaining a predicted reaction magnetic field for the reconstructed new position from the reaction field model, obtaining a compensated measurement by subtracting the predicted reaction magnetic field from the second measurements, adjusting the first measurements according to the compensated measurement, and calculating a position of the probe magnetic field sensor using the adjusted first measurements.

According to one aspect of the method, obtaining a compensated measurement includes defining a cost function based on a difference between the second measurements and the predicted reaction magnetic field, minimizing the cost function by finding optimum values of parameters of the perturbed magnetic field obtained in the second measurements, and defining an optimized reaction field from the optimum values of the parameters.

According to one aspect of the method, the parameters comprise three location parameters and three orientation parameters of the location sensor.

According to a further aspect of the method, the location sensor includes an group of three location sensors, and wherein obtaining second measurements from the three location sensors includes determining 25 output parameters, and wherein defining an optimized reaction field includes varying the 25 output parameters.

According to a further aspect of the method, adjusting the first measurements includes subtracting the optimized reaction field from the first measurements.

According to an additional aspect of the method, adjusting the first measurements also includes characterizing the first measurements as a spatial transfer matrix between the field-perturbing element and a location of the location sensor, characterizing the optimized reaction field as a reaction field matrix, and calculating a product of the spatial transfer matrix and the reaction field matrix.

According to yet another aspect of the method, the perturbing element includes a fluoroscope detector and a fluoroscope collimator, and characterizing the optimized reaction field as a reaction field matrix includes calculating the reaction field matrix as a product of a first matrix of estimated magnetic field values at a plurality of satellite points of the fluoroscope detector and a second matrix of estimated magnetic field values at a plurality of second satellite points of the fluoroscope collimator.

According to still another aspect of the method, the first matrix is multiplied by a first matrix of constants whose values characterize a reaction field model of the fluoroscope detector and the second matrix is multiplied by a second matrix of constants whose values characterize a reaction model of the fluoroscope collimator to define a first matrix product and a second matrix product, respectively.

According to an additional aspect of the method, the first matrix product and the second matrix product comprise multipole coefficients.

In another aspect of the method, obtaining a compensated measurement is performed using an instance of the predicted reaction magnetic field that was obtained in a preceding performance of reconstructing the new position and obtaining a predicted reaction magnetic field.

According to yet another aspect of the method, creating a reaction field model includes characterizing multiple images of magnetic transmitters in the field-perturbing element, and calculating the reaction magnetic field in the region based on the characterized images.

According to still another aspect of the method, calculating the reaction magnetic field is performed using a spherical harmonic expansion.

According to an aspect of the method, creating a reaction field model includes characterizing the respective reaction magnetic fields of the reaction field model as including parameters of location and orientation of the field-perturbing element with six degrees of freedom.

There is further provided according to embodiments of the invention an apparatus, including a plurality of magnetic field generators for generating a magnetic field in a region, a field-perturbing element in the region, a magnetic field location sensor disposed between the field-perturbing element and the magnetic field generators, and a processor, which is configured for creating a reaction field model by calculating respective reaction magnetic fields while the field-perturbing element is in known positions. In operation, the field-perturbing element is placed in a new position within the region and a distal segment of a probe having a probe magnetic field sensor thereon is introduced into the region. The processor is further configured for obtaining first measurements of a perturbed magnetic field produced by the magnetic field generators from the probe magnetic field sensor, obtaining second measurements of the perturbed magnetic field from the location sensor, reconstructing the new position of the field-perturbing element from the second measurements, obtaining a predicted reaction magnetic field for the reconstructed new position from the reaction field model, obtaining a compensated measurement by subtracting the predicted reaction magnetic field from the second measurements, adjusting the first measurements according to the compensated measurement, and calculating a position of the probe magnetic field sensor using the adjusted first measurements.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein:

FIG. 7 is an equation, which is formulated in accordance with an embodiment of the invention;

FIG. 8 is a matrix equation, which is formulated in accordance with an embodiment of the invention;

FIG. 12 is an equation, which is formulated in accordance with an embodiment of the invention;

FIG. 13 is an equation, which is formulated in accordance with an embodiment of the invention;

FIG. 14 is an equation, which is formulated in accordance with an embodiment of the invention;

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Overview.

Embodiments of the present invention provide a method for compensating for perturbations created in a magnetic field in a region of interest. The perturbations are caused by introduction of a field-perturbing element, typically a metallic component, into a field generated by magnetic transmitters. In one aspect of the invention, an easily calculable, mathematical estimation of the interference magnetic field caused by a fluoroscope is obtained. The estimated interference field is subtracted from the measurements obtained from magnetic sensors of the magnetic tracking system to obtain corrected measurements. The corrected measurements are used to calculate the true location and orientation of the sensor.

In this disclosure, the interference fields generated by eddy currents in the perturbing element are treated using a reaction field model. In order to compensate for the presence of the perturbing element, the reaction field model assumes that each magnetic transmitter of the magnetic tracking system creates multiple images of the transmitter in the perturbing element. The reaction field model assumes that each image generates a respective reaction field, which in total act to perturb the field generated by the transmitters.

Each image may typically be characterized as a combination of multipoles, i.e., dipoles, quadrupoles and/or higher order poles. Characteristics of each image are also dependent, inter alia, on the transmitter field generating the image. The reaction field model typically calculates the reaction field from each of the multipolar images by assuming that the field can be represented by a spherical harmonic expansion, and according to characteristics of the images. The reaction field model is described in further detail below.

Figure 1:
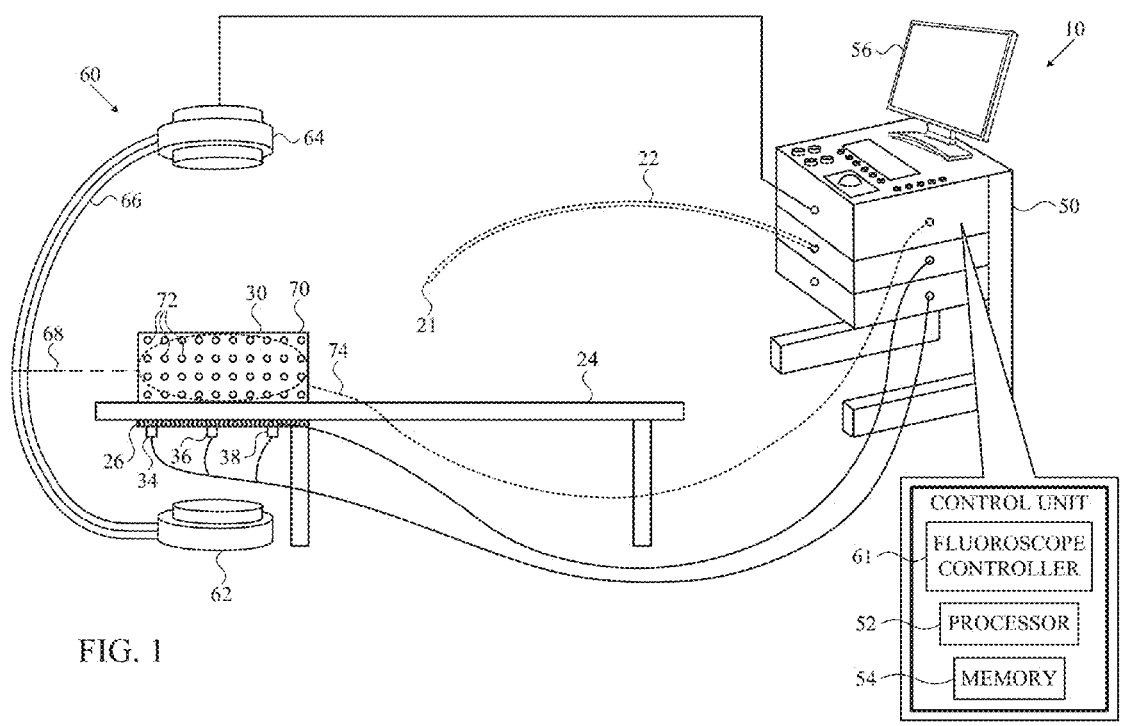
FIG. 1 is a schematic, pictorial illustration of a position sensing system in accordance with an embodiment of the invention.

Turning now to the drawings, Reference is initially made to FIG. 1, which is a schematic, pictorial illustration of a position sensing system 10, which is configured to sense the position of a distal end 21 of a catheter probe 22 in accordance with an embodiment of the invention. Typically, the probe 22 is inserted into a body cavity or organ of a patient by a medical professional during an operational phase of system 10, and is not present during a calibration phase of the system. For clarity, probe 22 is shown in FIG. 1 with broken lines. The patient typically lies on an operating table 24 in a magnetic field during a procedure performed by the medical professional, who may operate position-sensing system 10. The magnetic field is generated by positioning, under the patient, a location pad 26 which is an assembly of generally similar alternating magnetic field generators 34, 36, 38, each of the field generators having three field generating coils, so that the location pad 26 comprises a total of nine generating coils. The magnetic field generators 34, 36, 38 generate alternating magnetic fields in a region 30, schematically illustrated as an ellipse. The magnetic field generators 34, 36, 38 may be distinguished by operation at different frequencies or by time multiplexing. For clarity and simplicity, neither the patient nor the medical professional is shown in FIG. 1.

The system 10 employs a control unit 50, which includes a processor 52, typically a computer with appropriate signal processing circuits. The processor uses a memory 54, which typically comprises both volatile and non-volatile data storage devices, wherein data for operating system 10 is stored. The processor is coupled to drive a console, which may provide a visual display 56 of the location of probe 22.

System 10 includes a fluoroscope 60, which is operated by a fluoroscope controller 61, and which is able to produce fluoroscopic images of the patient on the operating table 24. Fluoroscope controller 61 is shown as a sub-unit of control unit 50; however, it may be implemented separately from the control unit 50. Fluoroscope 60 has a number of sections, comprising a collimated X-ray source, referred to herein as collimator 62, and a detector 64. The collimator 62 and the detector 64 are connected together by another section, a C-arm 66, which allows them to be rotated about two axes, a horizontal axis 68, and an axis perpendicular to the plane of the paper through axis 68. The C-arm 66 also allows the collimator 62 and detector 64 to be translated in space, such as in a direction parallel to the horizontal axis 68. C-arm 66 maintains the collimator 62 and detector 64 in a fixed alignment with each other, and at a constant distance from each other, during rotation of the fluoroscope 60 about axis 68. Typically, the images formed by fluoroscope 60 may be formed with the fluoroscope 60 rotated to any orientation about the horizontal axis 68, the orientation being selected according to the needs of the patient and the requirements of the professional operating the system 10.

Typically, fluoroscope 60 operates to produce its images at substantially the same time as probe 22 is being used. However, metallic components of the fluoroscope 60, which are in proximity to region 30, alter the magnetic fields generated by magnetic field generators 34, 36, 38 in the region 30. As noted above, without compensation for these alterations, inaccuracies in the measured location of probe 22 are introduced. As described herein, embodiments of the present invention compensate for the field perturbations produced by fluoroscope 60, regardless of the orientation or position of the fluoroscope 60 relative to table 24, thus preventing any inaccuracies in the measured location of the probe 22.

Typically, the system 10 includes other elements, which are not shown in the figures for the sake of simplicity, and which are referred to as necessary in the following description. For example, system 10 may include an ECG monitor, coupled to receive signals from one or more body surface electrodes, so as to provide an ECG synchronization signal to control unit 50.

The configuration of FIG. 1 is an exemplary configuration, which is chosen purely for the sake of conceptual clarity. In alternative embodiments, any other suitable configuration can also be used. Typically, processor 52 is programmed in software to carry out the functions described herein. The software may be downloaded to the processor in electronic form, over a network, for example, or it may, alternatively or additionally, be provided and/or stored on nontransitory tangible media, such as magnetic, optical, or electronic memory.

System 10 also comprises apparatus, which is able to plot the magnetic fields that are generated by the magnetic field generators 34, 36, 38 in the region 30. In one embodiment of the present invention, a mapper 70 is used to plot the magnetic fields, the mapper comprising an array of magnetic field detectors 72, which are fixedly mounted in known positions on solid bases, such as sheets of plastic. Mapper 70 is configured so that it may be positioned on the operating table 24 in a known predetermined position and orientation relative to location pad 26. In one embodiment, mapper 70 comprises 72 detectors. Typically, the detectors are configured in the mapper 70 so that the magnetic field and all its non-negligible gradients are measurable. In an alternative embodiment, the mapper has 78 detectors distributed in a rectangular box having approximate dimensions of 150× 250×250 mm.

The mapper 70 may be positioned, typically approximately centrally with respect to left and right, and head and foot, using magnetic measurements from the magnetic field detectors 72.

Although in the following description of the operation of system 10 it is assumed that mapper 70 is used to plot magnetic fields, it will be understood that the mapper is an exemplary system for measuring the magnetic fields in region 30, and any other suitable system, such as one or more field detectors that may be moved into known positions, may be used. Such alternative field plotting systems will be apparent to those having ordinary skill in the art, and are assumed to be within the scope of the present invention.

Magnetic field detectors 72 may comprise any convenient tri-axial sensors for measuring the magnitude and direction of a magnetic field, such as Hall effect probes or sensors generally similar to sensor 46. The readings of such sensors may be represented as 3-element column vectors in a 3-dimensional coordinate system. The three magnetic field generators 34, 36, 38 of the location pad 26 have nine transmitting coils in total. Consequently, each of the magnetic field detectors 72 responds to magnetic fields comprising 9×3=27 input parameters. As will be seen from the discussion below the output of the three-dimensional sensor assembly in the location pad 26 comprises 18 location and orientation output parameters when there are nine magnetic field coils as in the system 10. The readings from the magnetic field detectors 72 are transferred to control unit 50, typically by a connecting cable 74, although any other convenient transfer method may be used, such as wireless transmission.

As described in more detail below, mapper 70 is used in during calibration of system 10, so that the mapper 70 and the cable 74 are shown in broken lines. The mapper 70 and cable 74 are removed when system 10 is in its operational phase.

Figure 2:
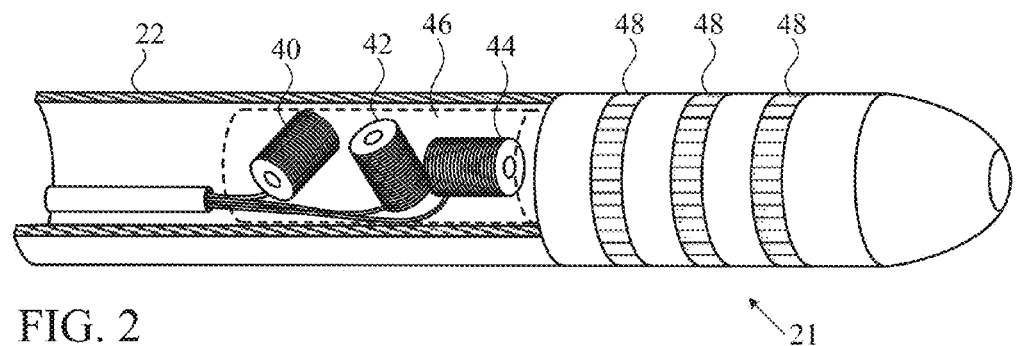
FIG. 2 is a schematic detailed view showing the distal end of a probe in the system shown in FIG. 1, in accordance with an embodiment of the invention.

Reference is now made to FIG. 2, which is a schematic detailed view showing the distal end 21 (FIG. 1), in accordance with an embodiment of the invention. Distal end 21 comprises three generally orthogonal coils 40, 42, 44 as part of an electromagnetic sensor 46. The distal end 21 typically comprises other elements, such as ablation or mapping electrodes 48. The magnetic fields generated by magnetic field generators 34, 36, 38 produce electrical signals in the coils of sensor 46, according to the fields sensed by the coils. The electrical signals from the coils of sensor 46 are conveyed to the control unit 50, which analyzes the signals so as to determine the coordinates of the position and of the orientation of probe 22. The coordinates may be referenced to a set of orthogonal xyz axes.

Other arrangements of coils in distal end 21, for detecting the position and orientation of probe 22, are known in the art. One such arrangement uses one coil, which measures projections of fields. Those having ordinary skill in the art will be able to adapt the present description, mutatis mutandis, to account for coil arrangements different from the one exemplified by coils 40, 42, and 44.

Reaction Field Model.

Figure 3:
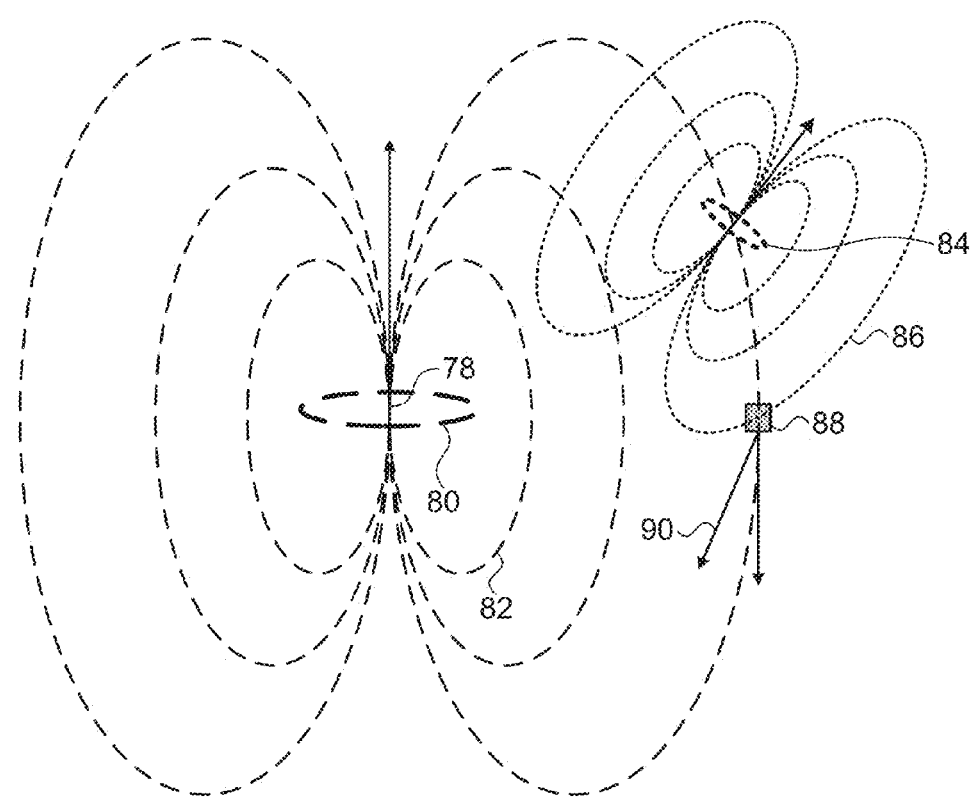
FIG. 3 is a diagram illustrating magnetic fields, which are evaluated in accordance with an embodiment of the invention.

One reaction field model is known from the above-mentioned U.S. Patent Application Publication No. 2012/0165656 to Montag. The following description of the reaction field model will facilitate understanding of the principles of the invention Reference is now made to FIG. 3, which is a diagram illustrating magnetic fields, which are evaluated in accordance with an embodiment of the invention. The basic physics behind the reaction field model is that oscillating magnetic fields induce electric currents in any conductor. The simplest possible configuration is shown in FIG. 3. A source 78, e.g., one of the magnetic field generators 34, 36, 38 in the system 10 (FIG. 1), produces a source loop 80 of oscillating current which produces a time-varying magnetic field (source field 82 represented by dotted lines). The source field 82 creates a time-varying flux in a nearby conducting loop 84. According to Ampere's law, a time varying magnetic flux causes an electric current, which in turn generates a magnetic field (reaction field 86 represented by dashed lines) that interferes with the source field 82. A sensor 88 will experience a measured field (shown as vector 90), which is the superposition of the source field 82 and the reaction field 86. The magnetic location algorithms employed by magnetic tracking systems typically are based on comparing the measured field of the sensor 88 with a known field configuration from the source 78. Any measurement interference will cause errors in the location and orientation.

If the source loop 80 is oscillating at a steady frequency, we can regard an expression for the amplitude of the induced field as a solution to a static problem. The general form of the reaction field model is a linear equation.

$$B_{reaction}(x,y,z)=T_{spatial}(x,y,z)\cdot T_{reaction}\cdot B_{transmitted} \quad (1)$$

$B_{reaction}(x,y,z)$ represents the (vector) amplitude of the induced reaction field, at any point in space. $B_{transmitted}$ represents the source field.

$T_{reaction}$ is the reaction matrix.

The physical properties of the reaction loop are contained in $T_{reaction}$. In the case at hand, this is the area of the loop. The implicit frequency dependence is also contained in this term. $T_{spatial}(x,y,z)$ is the connection from what happens at the sensor coil to any point in space. If we approximate the reacting loop to be a dipole source, we have the well-known formula $$B(m,r) = \frac{\mu_0}{4\pi r^3}(3(m\cdot\hat{r})\hat{r} - m) + \frac{2\mu_0}{3}m\delta^3(r) \quad (2)$$

In Equation (2) m represents $T_{reaction}\cdot B_{transmitted}$, and the rest of the equation represents $T_{spatial}(x,y,z)$ of Equation (1), with r=(x,y,z).

It will be apparent from the above discussion that the reaction field characterizes the location and orientation of the field-perturbing element with six degrees of freedom.

The real world, reaction field is not caused by a simple conducting loop, but rather large metallic objects, most significantly in the context of the present invention, the source-collimator and detector assemblies of the fluoroscope 60. In this case finding a mathematical solution for the response is a much more complicated task.

Adaptive FER Algorithm Summary.

The fluoroscope effect on CARTO measurements is an additive field reacting to the generated field produced by the CARTO System. When the location and reaction field model of the fluoroscope is known, the reaction can be negated and accuracy of measurement in the CARTO magnetic tracking system restored.

The adaptive FER reconstructs the fluoroscope location from measurements taken from location patch sensors (sometimes referred to herein as "chest sensors") having magnetic sensors on the subject's chest. A tri-axial sensor measurement yields 9 magnetic vector fields, or 27 numbers. These are used to find the three location parameters and three orientation parameters. Clearly, there is a high level of redundancy in the system. We have found that by taking three location patch sensors together, we can create a mathematical model for the expected measurements, which includes the 6*3=18 sensor parameters as well as 7 CARTO-Fluoroscope coordinate transfer parameters. These 18+7=25 parameters are referred to as "output parameters"). We perform an optimization on the difference between the mathematical model and a set of actual measurements to find the fluoroscope position. This requires no advanced knowledge of the sensor location or the fluoroscope pose. There is also no assumption that the location patch sensors remain stationary or have any constant relative location.

Generically, the reaction field of one of the magnetic field detectors 72 can be described by an equation $$estM_{LP}(x,y,z,\alpha,\beta,\gamma)=rot(\alpha,\beta,\gamma)[\text{s.h. polynomials}][\text{coeficients}],$$

wherein $rot(\alpha,\beta,\gamma)$ is a rotation matrix, s.h. polynomials are spherical harmonic polynomials about the centers of the coils of the magnetic field generators 34, 36, 38 field generating coils, and coefficients are numerical constants describing the field source.

A reaction field produced by the detector 64 in one of the magnetic field detectors 72 can be estimated $$estM_{Det}(x,y,z)=rot(\phi,\theta,\psi)[\text{s.h. polynomials}][\text{coefficients}_{Det}]\cdot(x,y,z)-\text{CARTO Points}$$

where $rot(\phi,\theta,\psi)$ represents rotation between the CARTO magnetic field detector and the fluoroscope detector coordinate systems The centers of the spherical harmonics (also known as "expansion points") may be selected according to the teachings of the above-referenced U.S. Patent Application Publication No. 2012/0165656.

Thus, in the case of 3 location patch sensors there are 81 input numbers to find (3×6)+7=25 unknowns. The term s.h. polynomials has the same meaning as in the previous equation, and $$[\text{coefficients}_{Det}]=[T_{Det}^{Reac}][B_{Det}^{Sat}]$$

$[B_{Det}^{Sat}]$ is the estimated LP field at detector satellite points. $[T_{Det}^{Reac}]$ is the detector reaction field matrix, which is computed from a reaction field model. Satellite points and the reaction field model are described below.

A similar equation may be written in order to estimate the reaction field produced by the collimator 62.

In the case of the system 10, the estimated reaction field experienced by a magnetic field sensor is the additive field effect of the estimated reaction fields of the detector 64 and the collimator 62:

$$estM^{Reac}(x,y,z)=estM_{Det}(x,y,z)+estM_{Coll}(x,y,z)$$

Thus, for a location patch sensor k, $$estMeas_{Adap}{}^{k}=estM_{LP}(x_k,y_k,z_k,\alpha_k,\beta_k,\gamma_k)+ rot(\alpha^k,\beta^k,\gamma^k)\cdot estM^{Reac}(x_k,y_k,z_k,x_{CARTO}{}^{Fluoro}, y_{CARTO}{}^{Fluoro},z_{CARTO}{}^{Det},z_{CARTO}{}^{Coll},\phi,\theta,\psi)$$

Because the C-Arm forces joint movement of the detector and collimator, there are 7 independent parameters: 3 rotation angles; x- and y-offsets of fluoroscope center of rotation; z-offset of detector (varies with SID); and z-offset of the collimator:

$$estM^{Reac}(x_{CARTO},y_{CARTO},z_{CARTO},x_{CARTO}{}^{Fluoro}, y_{CARTO}{}^{Fluoro},z_{CARTO}{}^{Det},z_{CARTO}{}^{Coll},\phi,\theta,\psi)$$

Once the 7 fluoroscope transfer parameters are known, they can be used in the Fluoroscopic Effect Reduction (FER) application disclosed in the above-referenced U.S. Patent Application Publication No. 2012/0165656 in order to compensate for magnetic sensors in a catheter within a subject.

In the system 10 measurements are obtained from magnetic sensors at frequent intervals, typically at 16 ms intervals. A measurement i is adjusted using the rotational parameters and reaction field that were estimated in the previous measurement i−1.

$$Meas_{FER}{}^{i}=Meas^{i}-rot(\alpha^{i-1},\beta^{i-1},\gamma^{i-1})\cdot estM^{Reac}(x^{i-1},y^{i-1},z^{i-1})$$

In the case of a single axis sensor, the rotation matrix term is replaced by vectors $(v_x^{i-1},v_y^{i-1},v_z^{i-1})$.

In an embodiment employing three location sensors the vector of differences between the estimated and measured magnetic fields is $$\Delta Field=(Meas_1,Meas_2,Meas_3)- (estMeas_{Adap}{}^{1},estMeas_{Adap}{}^{2},estMeas_{Adap}{}^{3})$$

where $Meas_i$ is the $i^{th}$ measured fields in sensor i and $estMeas_{Adap}{}^{i}$ is the $i^{th}$ estimated field.

A cost function $\Delta Field \cdot \Delta Field$ is then minimized, yielding a simultaneous solution for the sensor and fluoroscope magnetic field parameters. It will be recalled from the preceding discussion that in the case where three location sensors are used, each tri-axial location sensor measures 27 numbers—a three-dimensional vector for each of the nine 9 transmitting coils in the three magnetic field generators (in the example of FIG. 1). Reading all three location sensors involves 81 input parameters and 25 output parameters. The output parameters are varied in the minimization of the cost function. The input parameters are not varied. The cost function maps the values of the parameters of the measured and estimated magnetic fields to a real number. Minimization of the cost function minimizes the penalty for an incorrect determination. Many optimization methods suitable for the minimization are known. The Levenberg-Marquardt variant of the Gauss Newton Method is used in one embodiment. This technique is robust and convenient for implementations in programs such as Mathematica®, available from Wolfram Research, 100 Trade Center Drive, Champaign, Ill. 61820-7237, and in programming languages such as C and C++.

Figure 4:
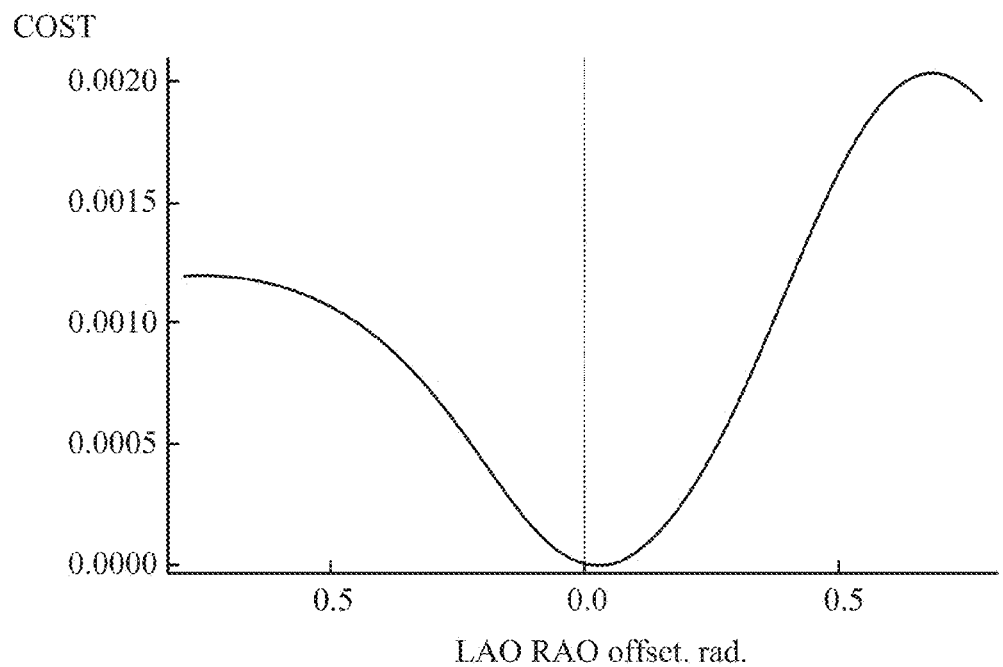
FIG. 4 is a data plot illustrating the effect on the cost function while varying some parameters.

Reference is now made to FIG. 4, which is a data plot illustrating the effect on the cost function while varying the rotational LAO-RAO fluoroscopic parameters (shown above as rot($\alpha,\beta,\gamma$)). A local minimum is clearly identified.

Figure 5:
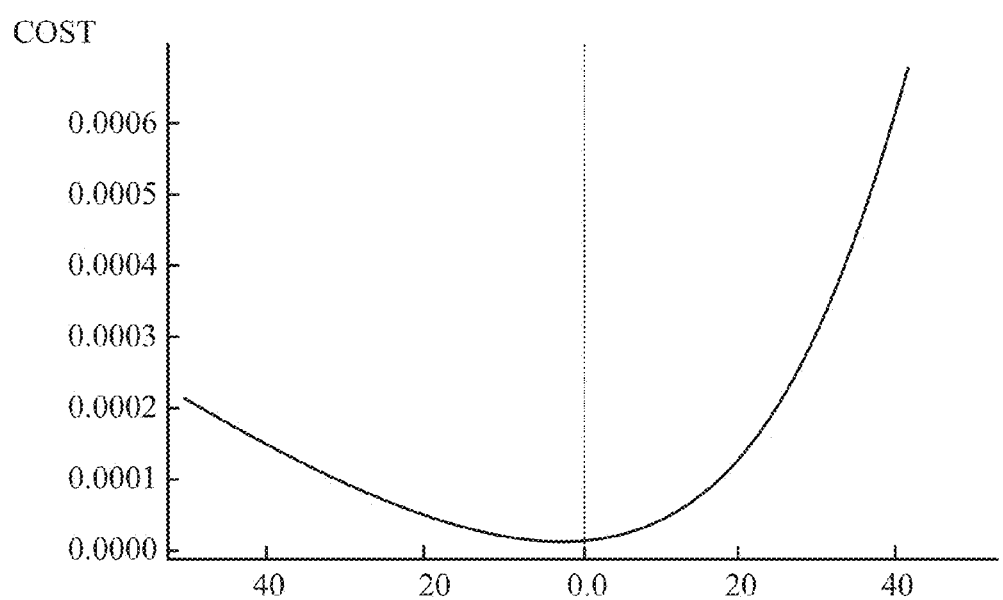
FIG. 5 is another data plot illustrating the effect on the cost function of varying some parameters.

Reference is now made to FIG. 5, which is a data plot illustrating the effect on the cost function while varying the SID offset parameter. While the cost function is less sensitive to variations in this parameter, a broad minimum is nevertheless identified.

Three location patch sensors were chosen in a current embodiment for convenience. A larger number can be used, in which case there will be further overdetermination of the solutions, with some improvement in accuracy, the tradeoff being the cost in computer resources and execution time. Fewer than three locations, indeed even one location sensor would yield a solution. While the latter choices would result in decreased cost and complexity, they would be expected to yield suboptimal results. Table 2 illustrates the effect of varying the number of location sensors.

TABLE 2

| Sensors | Input Numbers | Unknowns |
|---|---|---|
| 4 | (4 × 27) = 108 | (24 + 7) = 31 |
| 3 | (3 × 27) = 81 | (18 + 7) = 25 |
| 2 | (2 × 27) = 54 | (12 + 7) = 19 |
| 1 | (1 × 27) = 27 | (6 + 7) = 13 |

Further alternatively, one or more of the location patch sensors might be replaced by the sensor coils in the catheter itself. It has been found, however, that the method works best when the interference is strongest. Chest patch sensors are closer to the detector than the catheter electrodes, and the reaction field is more sensitive to the detector position in particular. The adaptive FER algorithm is also sensitive to the collimator position, but because the transmitting coils are between the collimator and the sensors, the relative interference from the collimator is independent of the height of the sensor above the collimator. At most the catheter sensor would be expected to contribute some useful information when the fluoroscope detector face is vertical, i.e., directed to the side of the patient. In this extreme position, only one or two of the chest patch sensors contribute much useful information. The catheter sensor, being in a different vertical plane, might offer some limited additional information.

Analytic Simulation of Reaction Field.

To find an approach for modeling the response of a large conducting object, it helps to consider the fundamental physics of the quasi-static electromagnetic field. The CARTO system broadcasts an electromagnetic field in the range of 1-4 kHz. If a conductor is placed in such an oscillating field, the magnetic field impinges on the conductor and induces an electric current. The displacement of the electric charges creates an electric field. The salient property of any conductor is that the free charges in the material start moving to counteract the induced electric field. The consequence is that the incident fields only penetrate to a depth of the order of $$\delta = \sqrt{\frac{1}{2\pi\mu\rho v}},$$

where μ is the magnetic permeability, σ is the conductivity, and ν is the frequency. For room temperature copper at 2 kHz, the result is about 1.5 mm, with similar results for other common conductors, such as aluminum. This is much smaller than the dimensions of the fluoroscope collimator and detector assemblies, meaning that the currents essentially flow on the surface, and we can act as if the current does not penetrate the surface at all. It also means that only the metal casing is significant as an interference source, but not the components inside. The reaction field is such that at the surface of the conducting body the normal component exactly cancels the normal component of the transmitted field. In effect, what happens is that the eddy currents tend to expel all magnetic fields from the inside of the conductor, just the way a superconductor expels magnetic fields from its interior. It is the reaction field outside the conductor that interferes with the measurements by the magnetic tracking system. These can be calculated by solving the corresponding static problem for a superconductor of the same shape. (Landau and Lifshitz, Electrodynamics of Continuous Media, section 45).

The above-noted CARTO system was used in the exemplary simulation. To obtain an analytic model that can teach us about the behavior of the reaction field in the CARTO system, we simulated the behavior of a super-conducting sphere of dimensions comparable to a fluoroscope in the magnetic field of a CARTO system taken to be static. We constructed a model of the reaction field using image magnetic charges as described in a paper by Lindell and Lehtola (IEEE Trans. Magnetics 128:4, 1992, pp 1930-1934).

Figure 6:
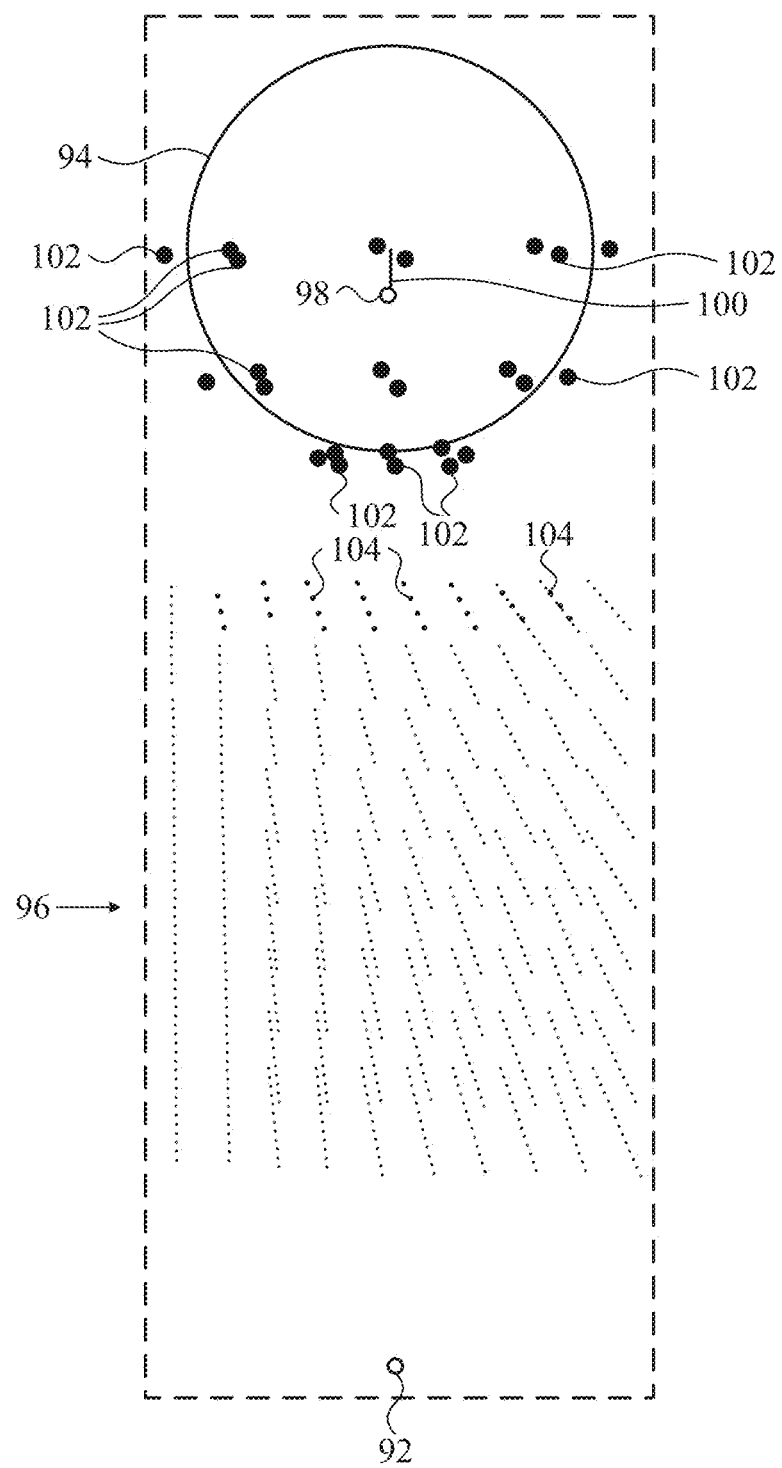
FIG. 6 is a diagram of an arrangement for simulating a reaction field, in accordance with an embodiment of the invention.

Reference is now made to FIG. 6, which is an abstracted diagram of an arrangement for simulating a reaction field, in accordance with an embodiment of the invention. A dot 92 on the bottom of the figure represents one of the magnetic field generators 34, 36, 38 of the location pad 26 (FIG. 1). A conducting sphere 94, an abstracted fluoroscope component, is above an imaging volume 96, represented by a grid of points. The reaction field in such a configuration is due to a complicated pattern of eddy currents flowing on the surface of the sphere 94. However, the reaction field can be modeled as coming from image magnetic sources: a point dipole source 98, which is the response to impinging transverse fields and a string of dipoles responding to axial fields. The dipoles are indicated by a linear symbol 100. The locations of the point dipole source and dipole strings are determined by the size of the sphere and distance from the transmitter. Its strength is a function of those dimensions and is proportional to the transmitted field strength. Since the image charge is a mathematical convenience, the details of the field inside the sphere 94 are of no interest.

The correspondence between this simulation and Equation (1) goes as follows. $B_{transmitted}$ represents the transmitted field in the vicinity of the large conducting object. In the example of FIG. 6, we construct a matrix whose values are the transmitter fields at points 102 that envelop the sphere 94. $T_{reaction}$ represents the magnetic response properties of the sphere 94, which are invariant with respect to the sphere location. For the moment, we leave this as a matrix of unknowns. $T_{spatial}(x,y,z)$ is a transfer function, which gives the field for any point in space relative to the location of the locations of the magnetic moments. We use the known field distribution for a dipole source for the point dipole component, and perform an integral over the magnetic field over a string of dipoles to get the string component to find their spatial functions in terms of the coordinates (x,y,z). In a frame of reference defined with respect to the center of the sphere 94 and with the z-axis in the direction between the sphere 94 and the transmitter, the product $T_{reaction} \cdot B_{transmitted}$ represents the magnetic moments of the image source elements. That means that the strength of the moments is linearly proportional to $B_{transmitted}$, which depends only on the location and orientation of the sphere with respect to the transmitters.

To test the concept, we used our a priori knowledge of the analytical solution to calculate the reaction field at a given set of points, shown in red. Reference is now made to FIG. 7, which is Equation (3), which is formulated in accordance with an embodiment of the invention. We solved for $T_{reaction}$ by moving it to the right side of the equation using the Kronecker product, wherein the notation "(red)" refers to points 104 (shown as small dots in FIG. 6 and "(blue)" to the points 102 (shown as larger dots). We verified that the product $T_{reaction} \cdot B_{transmitted}$ gave us back the same magnetic dipole moments as was put into the analytical solution.

Furthermore, we solved for $T_{reaction}$ simultaneously inputting information from a large set of sphere locations, concatenating several sets of $B_{transmitted}$ and $B_{reaction}$. Reference is now made to FIG. 8, which is Equation (4), in accordance with an embodiment of the invention. Equation (4) is a higher dimensional matrix equation, wherein Loc1 ... LocN refer to coordinates in mapping volume used by the CARTO, and the symbol T indicates a matrix transpose.

We then showed that to a high level of accuracy the product $T_{reaction} \cdot B_{transmitted}$ produced moments, which matched the analytic solution, for sphere locations not included in the set used to calculate $T_{reaction}$ That is, the same $T_{reaction}$ works with multiple $B_{satellite}$ sets. $B_{satellite}$ represents the source field evaluated at a point near the surface of the interference source, e.g., the points 102 (FIG. 6). The independence of $T_{reaction}$ and $B_{satellite}$ represents the proof of the concept.

Figure 9:
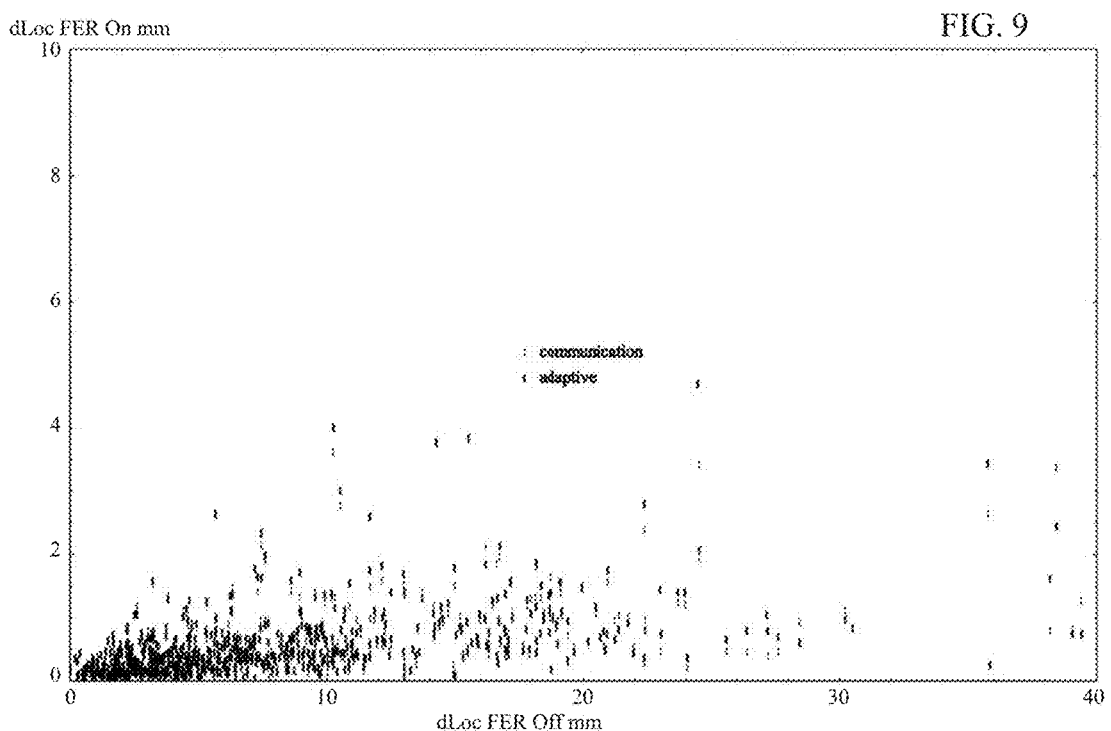
FIG. 9 is a graphical comparison of simulation results plotted against a standard FER technique, in accordance with an embodiment of the invention.

Reference is now made to FIG. 9, which is a graphical display of simulation results over an entire mapping volume plotted against a standard FER technique, in accordance with an embodiment of the invention. The x-axis represents uncorrected location errors, and the y-axis corrected location errors. Data using the FER and adaptive FER plotted, distinguished as shown in the key in FIG. 9. In the simulation, the fluoroscopic pose and resulting errors of the CARTO sensors were estimated. Source and interference data was simulated. When noise at a 5% level, i.e., spurious magnetic fields as may be produced by fluctuations in the currents in the magnetic field generators, is added to the simulation the FER and the simulated Adaptive FER performance are comparable.

Calibration.

Of course, none of the fluoroscope components whose eddy currents we need to compensate for is perfectly spherical. We need a more pragmatic approach in coming up with a mathematical model for the reaction field that strikes a balance between flexibility and specificity. Unlike the model for the spherical conductor, which has essentially no degrees of freedom, a practical model must have enough degrees of freedom to accurately describe complex patterns of reaction fields, but it must not have too many, or else solving for $T_{reaction}$ will lead to an over-determined solution that may diverge for fluoroscopic poses that are not in the set of fluoroscope configurations used to find the solution.

Our choice is to describe the reaction field based on a collection of magnetic multi-pole point sources. To describe the field of each source we use a spherical harmonic expansion. Spherical harmonic functions provide a complete basis for describing any static magnetic field in free space. The order of the spherical harmonic expansion we choose and the number of expansion centers represent the control of the degrees of freedom alluded to above. Thus, a practical reaction field model is produced by characterizing multiple images of each magnetic transmitter in the field-perturbing element and calculating a reaction magnetic field in the region based on the characterized images.

Our choices are guided by our experience with current loops and eddy currents. The field of a single circular current loop can be described analytically by a combination of elliptical functions. At a distance of several radii away from the center of the loop, the field can be accurately described by a dipole (the L=1 term in a spherical harmonics expansion). In the range of 1-4 radii, which is the approximate ratio of the distance between the metal components and CARTO mapping points and eddy current dimensions on the surface of the metal, we need to use larger values of L as explained below.

Figure 10:
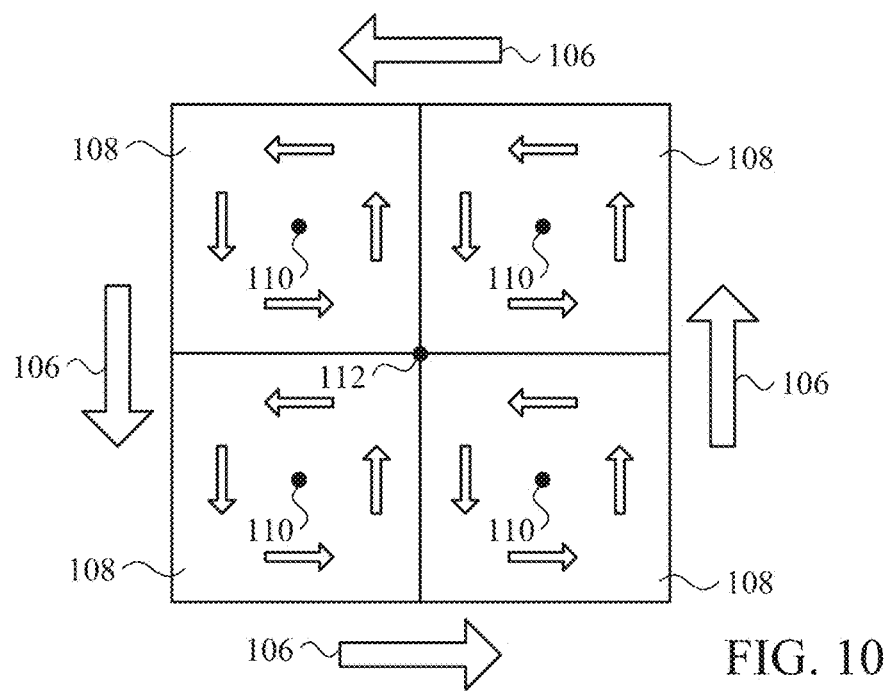
FIG. 10 is a schematic diagram showing eddy currents, in accordance with an embodiment of the invention.

Reference is now made to FIG. 10, which is a schematic diagram showing eddy currents, in accordance with an embodiment of the invention. FIG. 10 illustrates eddy currents the face of the detector 64 as well as the surface of the collimator 62 (FIG. 1). Arrows 106 about the periphery of the Figure represent a flow of current around the edge. Because currents flowing in opposite directions cancel out, this is mathematically equivalent to four current loops 108. The lengths of the radii of the current loops 108 are about the same as the distance of the detector from a catheter inside a patient when the fluoroscope is placed close to the patient's chest. The radius of the current loop represented by the arrows 106 is several times that distance. If we set centers of expansion for the spherical harmonics at centers 110 of each of the current loops 108, in addition to a fifth point 112 at the original center, we have found experimentally that we can get an accurate model of the reaction field using terms up to L=3 in the spherical harmonic expansion without over-determining the field.

Figure 11:
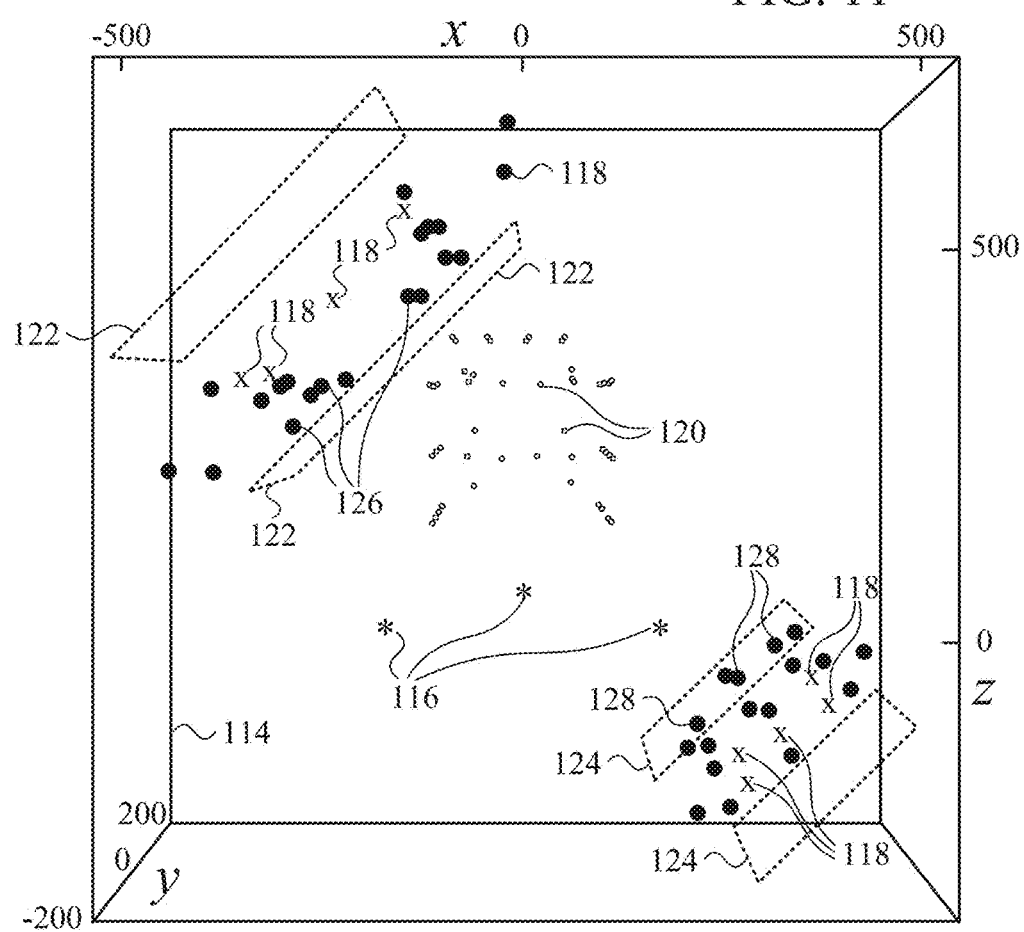
FIG. 11 is a schematic view of certain elements in the system shown in FIG. 1, in accordance with an embodiment of the invention.

Reference is now made to FIG. 11, which is a schematic view of essential elements shown in FIG. 1, in accordance with an embodiment of the invention. FIG. 11 represents the geometry of an actual experiment. With reference to a standard rectangular coordinate system 114, asterisks 116 respectively represent three concentric coils of the magnetic field generators, which lie on a triangle in the z=0 plane. Points 118 (indicated by large solid circles) are centers of expansion for the spherical harmonic functions. Points 120 (shown as small open circles) are selected points within the mapping volume. Rectangles 122, 124 represent the outlines of the fluoroscope detector 64 and surface of the collimator 62. Points 126, 128 (shown as larger solid dots) are sets of points surrounding the major metallic interference sources in the detector 64 and collimator 62. The basic assumption of the reaction method is that the response of the metal depends only on the value of the magnetic fields generated by the magnetic field generators in the location pad 26 (FIG. 1) at the points 126, 128. Because these points surround the metal and move along with them, they are referred to as "satellite points". The fields of the LP fields at these points are denoted $B_{satellite}$.

Reference is now made to FIG. 12, which is Equation (5) for $B_{reaction}$, in accordance with an embodiment of the invention. Equation (5) is similar to the simulation case described above. The major difference is that there are two sources of interference, each with its own $T_{reaction}$ matrix. In Equation (5) det refers to the detector (upper) side and col refers to the collimator (lower) side. The reaction field from each source at a given point is calculated in a coordinate system centered at that interference source, one of the points 118. The terms $(x_{det}, y_{det}, z_{det})$, $(x_{col}, y_{col}, z_{col})$ and $(x_{CARTO}, y_{CARTO}, z_{CARTO})$ all correspond to the same point. The symbol $Rot_{det/col}^{CARTO}$ represents a rotation matrix between the metal-centered coordinates to the CARTO coordinates. In operation, described below, equation (5) is applied to provide automatic dynamic tracking of changes in the transformations between the CARTO and fluoroscope coordinate systems without further registration procedures.

$T_{spatial}^{det/col}(x_{det/col}, y_{det/col}, z_{det/col})$ denotes the matrix spherical harmonics expansion polynomials in the metal-centered frame, and the product $[T_{reaction}^{det/col}] \cdot [B_{satellite}^{det/col}]$ form a matrix of the spherical harmonic coefficients. Whenever the fluoroscopic pose changes $B_{satellite}^{det/col}$ is updated.

Location and Orientation Correction.

Equation (5) gives the estimated reaction field for the location $(x_{CARTO}, y_{CARTO}, z_{CARTO})$. This location is not necessarily the true sensor location. Suppose a CARTO sensor's measurement is M. Applying the location and orientation algorithm give $r_{init}$ and $O_{init}$, an initial location and orientation. Equation (5) can be used to find a corrected measurement.

$$M_{corr} = M - O_{init} \cdot B_{reac}(r_{init}) \quad (6)$$

Equation (6) is the essence of the fluoroscopic effect reduction algorithm. We can get a corrected location and orientation by applying the CARTO location algorithm, which we will generically label LNO, to the corrected measurement, $M_{corr}$.

$$(r_{corr}, O_{corr}) = LNO(M_{corr}) \quad (7)$$

The measurements $r_{corr}$ and $O_{corr}$ can now be input into equation (6), replacing $r_{init}$ and $O_{init}$, to get a further refined corrected measurement. Because the reaction fields and their gradients are generally a few percent at most of the transmitted field, the values of r and O nearly always converge within four iterations to the same value that would have been reached if the correct sensor location and orientation has been put into equation (6) in the first place.

In the CARTO system implementation we do not work iteratively. Since a new measurement arrives every 16 milliseconds, we can think of the sensors as being effectively stationary, as if each measurement is a repeat of the previous one. We use the output of the previous LNO calculation (equation (7)) as the input to the current field correction:

$$M_{corr}^i = M^i - O^{i-1} B_{reac}(r^{i-1})$$

$$(r^i, O^i) = LNO(M_{corr}^i) \quad (8)$$

The first application of the FER algorithm after a system initiation or a fluoroscope move is performed using an LNO calculation on an uncorrected measurement.

Survey of a Fluoroscope to Determine $T_{reaction}$.

$T_{reaction}^{det}$ and $T_{reaction}^{col}$ are determined by a fluoroscope survey process. The first step is to perform a registration between the fluoroscope coordinate system and the CARTO coordinate system. Next, a fixed array of sensors, like the mapper 70 (FIG. 1), is placed on the patient bed. The sensor array covers a large section of the CARTO working volume. The fields are measured and recorded with the fluoroscope stowed. This provides a baseline measurement of both sensor locations and unperturbed transmitted field. Sets of measurements are then recorded with the fluoroscope set at various values of table height, SID, LAO-RAO angle, and optionally cranial-caudal angle. The measurement set should span all the clinical working positions of the fluoroscope. For each position and sensor the reaction field is calculated:

$$B_{reac}^{ij} = O^{i0} \cdot (M^{ij} - M^{i0}) \quad (9)$$

where i is an index over the sensors and j is an index over fluoroscope poses. j=0 indicates the fluoroscope is stowed.

To solve Equation (5) for both $T_{reaction}^{det}$ and $T_{reaction}^{col}$ simultaneously, we rearrange the terms by writing the analog of Equation (4) for the real situation. Reference is now made to FIG. 13, which is Equation (10), in accordance with an embodiment of the invention, which illustrates the rearrangement.

Reference is now made to FIG. 14, which is Equation (11), in accordance with an embodiment of the invention, and which illustrates combining matrices to eliminate the sum.

Before solving, we make one further modification. We weight $B_{reaction}$ and $B_{satellite}$ by the inverse of the transmitted field strength at their respective locations. In the CARTO coordinate system, the y-axis is directed from the heart center to the head, the x-axis from the heart center to the left arm, and the z-axis toward the ceiling. The weighting serves to increase the sensitivity of the solution at high-z. Equation (11) can be solved by multiplying both sides of the equation on the left by the pseudoinverse of the first matrix on the right side. The choice of tolerance in the pseudoinverse is important. Too small a tolerance can over-determine the solution. Too large a tolerance will lead to a suboptimal solution. To determine where to set the tolerance threshold, we started with a very small tolerance value of $1\times10^{-9}$ and gradually increased the value to a place where any further increase degraded the performance on the calibration data. Our current working value is $1\times10^{-6}$.

Once we have found the concatenation of $\text{vec}(T_{reaction}^{det})$ and $\text{vec}(T_{reaction}^{det})$ we can separate them and construct the two reaction matrices.

The FER algorithm described above has been implemented in Mathematica® and in C. The Mathematica implementation is used in the calibration procedure. The C implementation is used in clinical system operation.

Operation.

Figure 15:
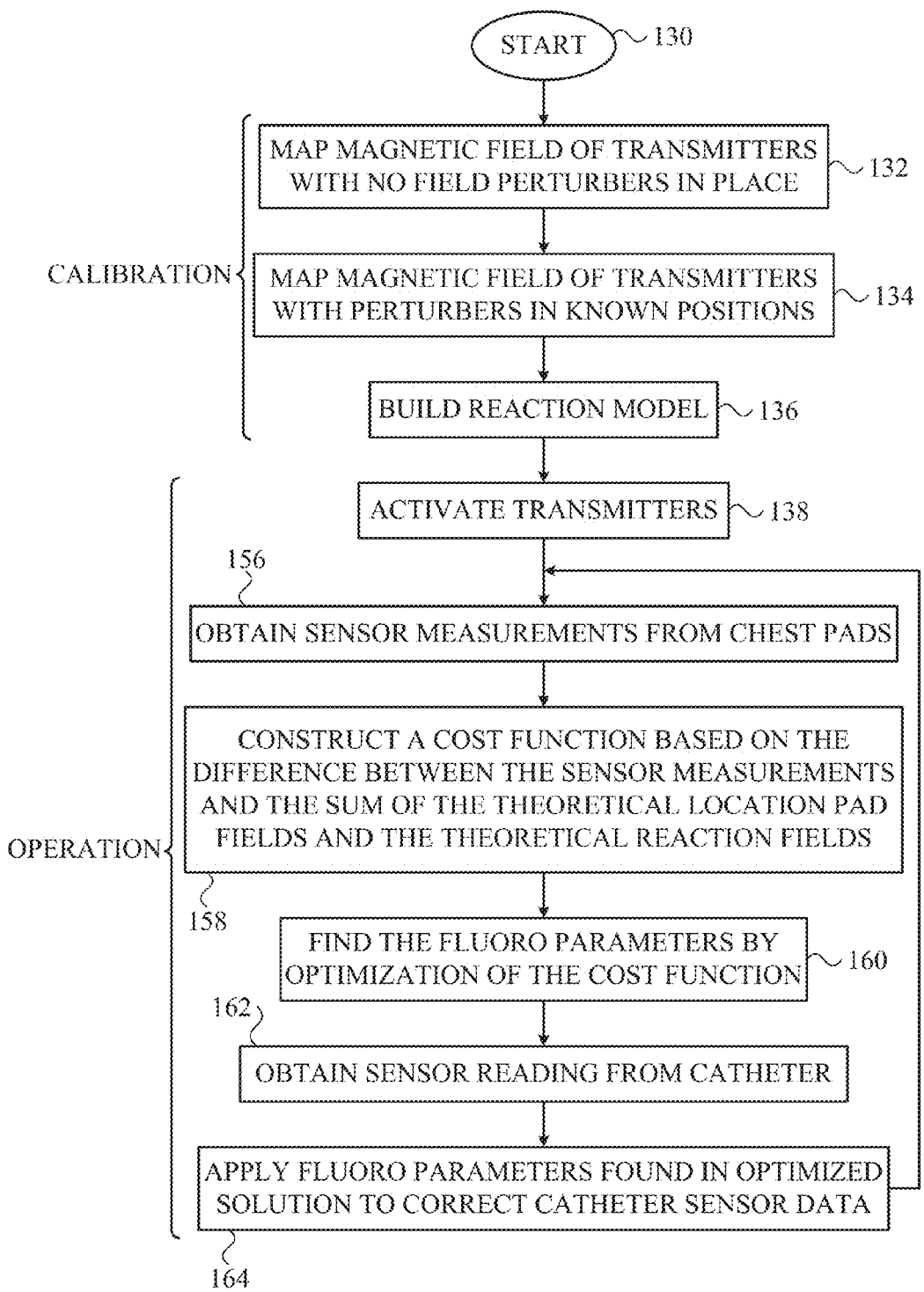
FIG. 15 is a flow chart of a method for compensating location-tracking errors of magnetic sensors due to field perturbation in accordance with an embodiment of the invention.

Reference is now made to FIG. 15, which is a flow chart of a method for compensating location tracking errors of magnetic sensors due to field perturbation in accordance with an embodiment of the invention. The process steps are shown in a particular linear sequence in FIG. 15 for clarity of presentation. However, it will be evident that many of them can be performed in parallel, asynchronously, or in different orders.

A calibration phase of the method begins at initial step 130, in which components are prepared, as shown in FIG. 1.

Next, at step 132, all objects that could perturb the field generated by the magnetic field generators 34, 36, 38 are removed from the region 30 and its vicinity. Such objects include the fluoroscope 60. The mapper 70 is positioned on the operating table 24 in its predetermined position and orientation relative to the location pad 26, and the magnetic field generators 34, 36, 38 are activated. Control unit 50 operates the magnetic field detectors 72 in order to calculate the location of the location pad sensors in an unperturbed magnetic field in region 30.

The control unit 50 accepts and processes readings from the magnetic field detectors 72.

Next, at step 134 the magnetic field is remapped with field-perturbing elements in place. This may be accomplished using the procedure described in the above-referenced U.S. Patent Application Publication No. 2012/0165656.

After completing step 134, at step 136 a reaction model for the particular fluoroscope collimator and detector is constructed as described above in the section entitled "Adaptive FER Algorithm Summary". Step 136 concludes the calibration phase. The calibration phase may only need to be performed when configuring a particular fluoroscope for use with a specific operating table and magnetic tracking system. In general, calibration need not be repeated between patient sessions unless there is some change in the geometry of the system, e.g., replacement of one of the fluoroscope components.

Figure 16:
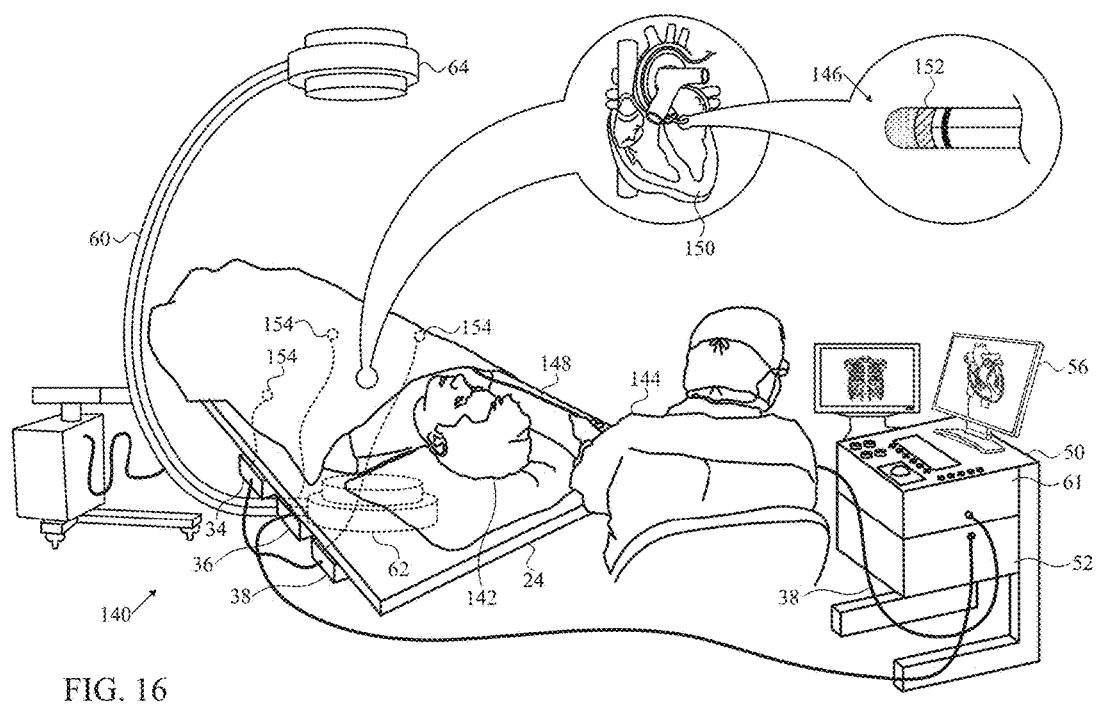
FIG. 16 schematically illustrates a system for tracking the end of a catheter, in accordance with an embodiment of the invention

An operational phase of the method begins at step 138. The magnetic field generators 34, 36, 38 are activated. Reference is now made to FIG. 16, which schematically illustrates a system 140 for tracking the end of a catheter, in accordance with an embodiment of the invention. The system 140 shares many components with the system 10 of FIG. 1, except now a catheterized subject 142 is on the operating table 24 instead of the mapper 70. An operator 144 navigates distal end 146 of a cardiac catheter 148 within heart 150. While the procedure is described with reference to one cardiac catheter, it is equally applicable when more than one catheter is used at the same time. It is the function of the magnetic tracking system to locate the distal end 146 based on signals provided by a magnetic sensor 152 on the distal segment of the catheter 148. Three magnetic sensors 154 are attached to the chest of the subject 142. The magnetic sensors 154 may have the same triaxial construction as the sensor 46 (FIG. 2).

Reverting to FIG. 15, the next steps essentially involve reconstructing the current position of the fluoroscope from measurements taken by the magnetic sensors 154, obtaining a predicted reaction magnetic field for the reconstructed position from the reaction field model, subtracting the predicted reaction magnetic field from the field measured by the magnetic sensors 154 to obtain a compensated measurement, and adjusting the field calculated from the readings of the magnetic sensor 152 by the compensated measurement. The adjusted field is used to calculate the actual position of the magnetic sensor 152.

At step 156 respective measurements of the perturbed magnetic field are taken repeatedly as described above with respect to calibration:

$$\text{Meas}_{FER}^{i} = \text{Meas}^{i} - \text{rot}(\alpha^{i-1}, \beta^{i-1}, \gamma^{i-1}) \cdot \text{est} M^{Reac}(x^{i-1}, y^{i-1}, z^{i-1})$$

Returning to FIG. 16, three chest sensors are shown in operating table 24, but as explained above, other numbers of sensors may be used. Chest sensors are convenient. The magnetic sensors 154 should be located closer to the detector that the collimator, as the reaction field is more sensitive to the position of the detector 64. The magnetic field generators 34, 36, 38 are between the collimator 62 and the magnetic sensors 154, so that the relative interference attributable to the collimator 62 is independent of the height of the magnetic sensors 154 above the collimator 62.

Alternatively, the magnetic sensors 154 may be positioned above the subject 142—between the subject 142 and the detector 64. This requires additional mounting facilities, and would be less convenient, but has the advantage of greater sensitivity to the perturbations produced by the detector 64. Indeed, the magnetic sensors 154 need not be in the same horizontal plane, but could be positioned in different planes. This arrangement would result in differential sensitivity of the magnetic sensors 154 to the collimator 62 and detector 64 in some positions of the fluoroscope 60.

Returning to FIG. 15, at step 158 a cost function based on the difference between the sensor measurements obtained in step 156 and the sum of the theoretical location pad and reaction fields of the reaction model developed in step 136. It will be recalled from the preceding discussion that this difference is calculated as $\Delta\text{Field}=(\text{Meas}_1 \text{ Meas}_2 \text{ Meas}_3)-$ (estMeas$_{Adap}^1$ estMeas$_{Adap}^2$ estMeas$_{Adap}^3$). One suitable cost function is ΔField·ΔField.

Next, at step 160 the fluoroscopic parameters (three rotation angles; x- and y-offsets of fluoroscope center of rotation; z-offset of detector, and z-offset of the collimator) are obtained by optimization of the cost function as described above.

Next, at step 162 magnetic sensor readings are obtained from the catheter 148 (FIG. 16) and an uncorrected position and orientation of the catheter tip obtained by the magnetic tracking system.

At step 164, The fluoroscopic parameters found in step 160 are applied to the uncorrected readings taken in step 162 in order to obtain a corrected position and orientation using the equations (5)-(11) as described above. Typically control returns to step 156 to iterate locating the tip of the catheter.

Validation Accuracy Summary

Figure 17:
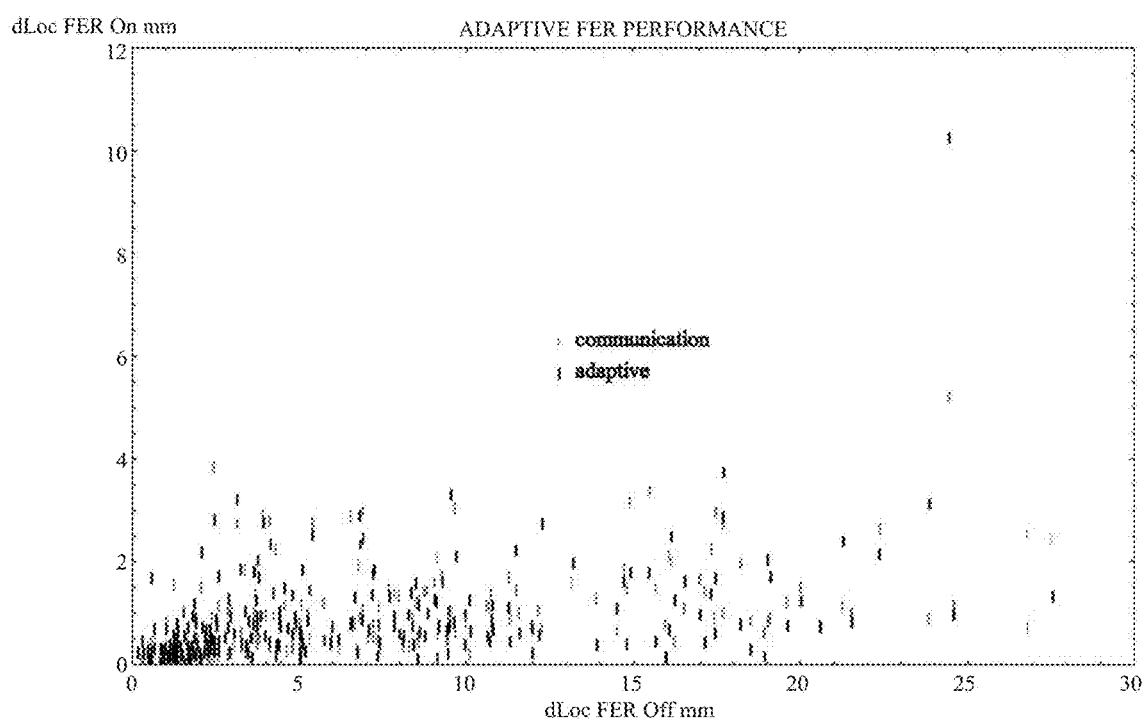
FIG. 17 is a graphical comparison plot of location error results obtained in accordance with an embodiment of the invention.

Reference is now made to FIG. 17, which is a data plot comparing location error results obtained using the adaptive FER and a standard FER method, in accordance with an embodiment of the invention. Three different fluoroscopes were employed: a Siemens, General Electric and Phillips models. It is that the adaptive FER performance approximates that of the standard FER the standard FER is labeled "communication" on the plot, because during operation the standard FER requires communication between the CARTO system and the fluoroscopic controller, whereas the adaptive FER does not.

Figure 18:
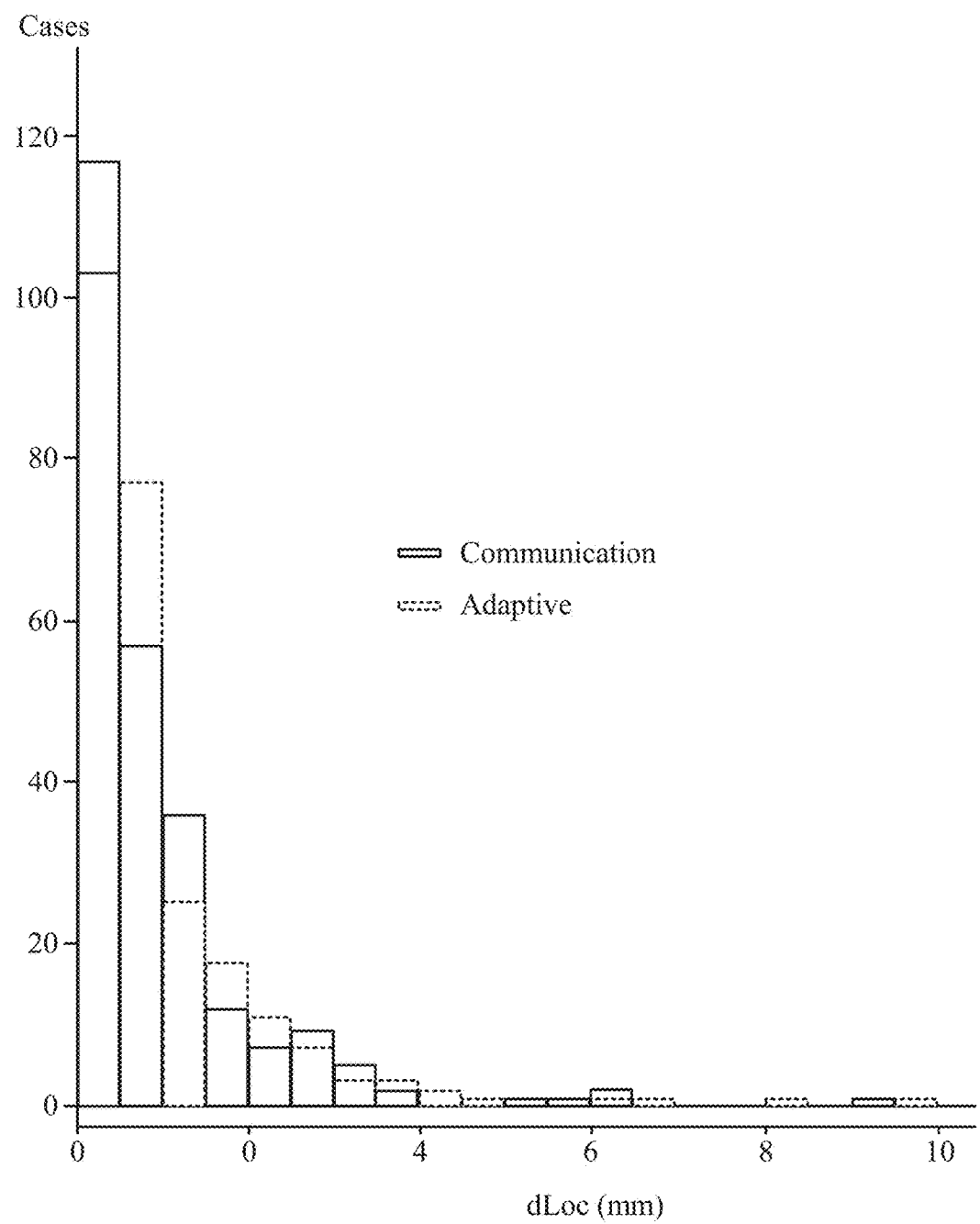
FIG. 18 is a comparative plot of location error distributions that were obtained in accordance with an embodiment of the invention.

Reference is now made to FIG. 18, which is a graphical plot comparing location error distributions using the conventional and adaptive FER, in accordance with an embodiment of the invention.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method, comprising the steps of:
   in a calibration phase performing the steps of:
   generating a magnetic field in a region using a plurality of magnetic field generators;
   placing a field-perturbing element in known positions within the region; and
   creating a reaction field model by calculating respective reaction magnetic fields while the field-perturbing element is in the known positions; and
   in an operational phase performing the steps of:
   placing the field-perturbing element in a new position within the region;
   disposing a magnetic field location sensor between the field-perturbing element and the magnetic field generators;
   introducing a distal segment of a probe into the region, a probe magnetic field sensor being disposed on the distal segment;
   regenerating a perturbed magnetic field with the magnetic field generators;
   obtaining first measurements of the perturbed magnetic field from the probe magnetic field sensor;
   obtaining second measurements of the perturbed magnetic field from the location sensor;
   reconstructing the new position of the field-perturbing element from the second measurements;
   obtaining a predicted reaction magnetic field for the reconstructed new position from the reaction field model;
   obtaining a compensated measurement by subtracting the predicted reaction magnetic field from the second measurements;
   adjusting the first measurements according to the compensated measurement; and
   calculating a position of the probe magnetic field sensor using the adjusted first measurements;
   wherein obtaining a compensated measurement comprises:
   defining a cost function based on a difference between the second measurements and the predicted reaction magnetic field;
   minimizing the cost function by finding optimum values of parameters of the perturbed magnetic field obtained in the second measurements; and
   defining an optimized reaction field having the optimum values of the parameters; and
   wherein the optimum values of parameters comprises fluoroscopic parameters representing three rotation angles; x- and y-offsets of fluoroscope center of rotation; z-offset of detector, and z-offset of the collimator and six location sensor parameters representing three rotation angles and x-, y- and z-offsets.

2. The method according to claim 1, wherein the parameters comprise three location parameters and three orientation parameters of the location sensor.

3. The method according to claim 1, wherein the location sensor comprises a group of three location sensors, and wherein obtaining second measurements from the three location sensors comprises determining 25 output parameters, and wherein defining an optimized reaction field comprises varying the 25 output parameters.

4. The method according to claim 1, wherein adjusting the first measurements comprises subtracting the optimized reaction field from the first measurements.

5. The method according to claim 1, wherein adjusting the first measurements further comprises:
   characterizing the first measurements as a spatial transfer matrix between the field-perturbing element and a location of the location sensor;
   characterizing the optimized reaction field as a reaction field matrix; and
   calculating a product of the spatial transfer matrix and the reaction field matrix.

6. The method according to claim 5, wherein the perturbing element comprises a fluoroscope detector and a fluoroscope collimator, and characterizing the optimized reaction field as a reaction field matrix comprises:
   calculating the reaction field matrix as a product of a first matrix of estimated magnetic field values at a plurality of satellite points of the fluoroscope detector and a second matrix of estimated magnetic field values at a plurality of second satellite points of the fluoroscope collimator.

7. The method according to claim 6, wherein the first matrix is multiplied by a first matrix of constants whose values characterize a reaction field model of the fluoroscope detector and the second matrix is multiplied by a second matrix of constants whose values characterize a reaction model of the fluoroscope collimator to define a first matrix product and a second matrix product, respectively.

8. The method according to claim 7, wherein the first matrix product and the second matrix product comprise multipole coefficients.

9. The method according to claim 1, wherein obtaining a compensated measurement is performed using an instance of the predicted reaction magnetic field that was obtained in a preceding performance of the steps of reconstructing the new position and obtaining a predicted reaction magnetic field.

10. The method according to claim 1, wherein creating a reaction field model comprises characterizing multiple images of magnetic transmitters in the field-perturbing element; and
calculating the reaction magnetic field in the region based on the characterized images.

11. The method according to claim 10, wherein calculating the reaction magnetic field is performed using a spherical harmonic expansion.

12. The method according to claim 1, wherein creating a reaction field model comprises characterizing the respective reaction magnetic fields of the reaction field model as comprising parameters of location and orientation of the field-perturbing element with six degrees of freedom.

13. An apparatus, comprising:
a plurality of magnetic field generators for generating a magnetic field in a region;
a field-perturbing element introduced into the region;
a magnetic field location sensor disposed between the field-perturbing element and the magnetic field generators;
and a processor, which is configured to perform the steps of:
creating a reaction field model by calculating respective reaction magnetic fields while the field-perturbing element is in known positions; and
when the field-perturbing element is placed in a new position within the region and when a distal segment of a probe having a probe magnetic field sensor is introduced into the region, performing the additional steps of:
obtaining first measurements of a perturbed magnetic field produced by the magnetic field generators from the probe magnetic field sensor;
obtaining second measurements of the perturbed magnetic field from the location sensor;
reconstructing the new position of the field-perturbing element from the second measurements;
obtaining a predicted reaction magnetic field for the reconstructed new position from the reaction field model;
obtaining a compensated measurement by subtracting the predicted reaction magnetic field from the second measurements;
adjusting the first measurements according to the compensated measurement; and
calculating a position of the probe magnetic field sensor using the adjusted first measurements;
wherein the processor is operative for obtaining a compensated measurement by:
defining a cost function based on a difference between the second measurements and the predicted reaction magnetic field;
minimizing the cost function by finding optimum values of parameters of the perturbed magnetic field obtained in the second measurements; and
defining an optimized reaction field having the optimum values of the parameters; and
wherein the optimum values of parameters comprises fluoroscopic parameters representing three rotation angles; x- and y-offsets of fluoroscope center of rotation; z-offset of detector, and z-offset of the collimator and six location sensor parameters representing three rotation angles and x-, y- and z-offsets.

14. The apparatus according to claim 13, wherein the parameters comprise three location parameters and three orientation parameters of the location sensor.

15. The apparatus according to claim 14, wherein the location sensor comprises an assembly of three location sensors, and wherein obtaining second measurements from the three location sensors comprises determining 25 output parameters, and wherein defining an optimized reaction field comprises varying the 25 output parameters.

16. The apparatus according to claim 13, wherein adjusting the first measurements comprises subtracting the optimized reaction field from the first measurements.

17. The apparatus according to claim 13, wherein adjusting the first measurements comprises:
characterizing the first measurements as a spatial transfer matrix between the field-perturbing element and a location of the location sensor;
characterizing the optimized reaction field as a reaction field matrix; and
calculating a product of the spatial transfer matrix and the reaction field matrix.

18. The apparatus according to claim 17, wherein the perturbing element comprises a fluoroscope detector and a fluoroscope collimator, and characterizing the optimized reaction field as a reaction field matrix comprises:
calculating the reaction field matrix as a product of a first matrix of estimated magnetic field values at a plurality of satellite points of the fluoroscope detector and a second matrix of estimated magnetic field values at a plurality of second satellite points of the fluoroscope collimator.

19. The apparatus according to claim 18, wherein the first matrix is multiplied by a first matrix of constants whose values characterize a reaction field model of the fluoroscope detector and the second matrix is multiplied by a second matrix of constants whose values characterize a reaction model of the fluoroscope collimator to define a first matrix product and a second matrix product, respectively.

20. The apparatus according to claim 13, wherein the processor is operative for obtaining a compensated measurement by using an instance of the predicted reaction magnetic field that was obtained in a preceding performance of the steps of reconstructing the new position and obtaining a predicted reaction magnetic field.

21. The apparatus according to claim 13, wherein creating a reaction field model comprises characterizing multiple images of magnetic transmitters in the field-perturbing element; and
calculating the reaction magnetic field in the region based on the characterized images.

22. The apparatus according to claim 21, wherein calculating the reaction magnetic field is performed using a spherical harmonic expansion.

23. The apparatus according to claim 13, wherein creating a reaction field model comprises characterizing the respective reaction magnetic fields of the reaction field model as comprising parameters of location and orientation of the field-perturbing element with six degrees of freedom.

* * * * *